(12) United States Patent
Speronello et al.

(10) Patent No.: US 8,311,625 B2
(45) Date of Patent: Nov. 13, 2012

(54) CHLORINE DIOXIDE TREATMENT FOR BIOLOGICAL TISSUE

(75) Inventors: Barry Keven Speronello, Montgomery Township, NJ (US); Linda Hratko, Colonia, NJ (US); Frank S. Castellana, Princeton, NJ (US); Andrew Patrick Full, Fanwood, NJ (US); Marcos Gomez, Princeton, NJ (US)

(73) Assignee: BASF Corporation, Florham Park, NJ (US)

(*) Notice: Subject to any disclaimer, the term of this patent is extended or adjusted under 35 U.S.C. 154(b) by 341 days.

(21) Appl. No.: 12/690,843

(22) Filed: Jan. 20, 2010

(65) Prior Publication Data

US 2010/0198136 A1 Aug. 5, 2010

Related U.S. Application Data

(60) Provisional application No. 61/149,784, filed on Feb. 4, 2009, provisional application No. 61/150,685, filed on Feb. 6, 2009, provisional application No. 61/187,198, filed on Jun. 15, 2009.

(51) Int. Cl.
*A61N 1/30* (2006.01)
(52) U.S. Cl. ......................................................... 604/20
(58) Field of Classification Search .................. 604/20, 604/500, 19; 424/443–445
See application file for complete search history.

(56) References Cited

U.S. PATENT DOCUMENTS

| | | |
|---|---|---|
| 2,071,091 A | 2/1937 | Taylor |
| 3,953,566 A | 4/1976 | Gore |
| 4,060,600 A | 11/1977 | Vit |
| 4,104,190 A | 8/1978 | Hartshorn |
| 4,330,531 A | 5/1982 | Alliger |
| 4,585,482 A | 4/1986 | Tice |
| 4,683,039 A | 7/1987 | Twardowski |
| 4,689,215 A | 8/1987 | Ratcliff |
| 4,696,811 A | 9/1987 | Ratcliff |
| 4,786,492 A | 11/1988 | Ratcliff |
| 4,788,053 A | 11/1988 | Ratcliff |
| 4,792,442 A | 12/1988 | Ratcliff |
| 4,793,989 A | 12/1988 | Ratcliff |
| 4,808,389 A | 2/1989 | Ratcliffe |
| 4,818,519 A | 4/1989 | Ratcliff |
| 4,832,009 A | 5/1989 | Dillon |
| 4,837,009 A | 6/1989 | Ractliff |
| 4,851,213 A | 7/1989 | Ratcliff |
| 4,855,135 A | 8/1989 | Ratcliff |
| 4,865,848 A | 9/1989 | Cheng |

(Continued)

FOREIGN PATENT DOCUMENTS

CN 00800063 2/2001

(Continued)

OTHER PUBLICATIONS

Anthony W. Smith, "Biofilms and antibiotic therapy: Is there a role for combating bacterial resistance by the use of novel drug delivery systems?", Advanced Drug Delivery Reviews, 2005 (Abstract Only).

(Continued)

*Primary Examiner* — Christopher D Koharski
(74) *Attorney, Agent, or Firm* — Bernard Lau

(57) ABSTRACT

Methods, compositions, devices, and systems for administration to a biological tissue of a composition comprising a chlorine dioxide source are provided.

17 Claims, 8 Drawing Sheets

U.S. PATENT DOCUMENTS

| | | | |
|---|---|---|---|
| 4,886,657 A | 12/1989 | Ratcliff | |
| 4,889,714 A | 12/1989 | Ratcliff | |
| 4,925,656 A | 5/1990 | Ratcliff | |
| 4,945,125 A | 7/1990 | Dillon | |
| 4,975,285 A | 12/1990 | Ratcliff | |
| 5,200,171 A | 4/1993 | Ratcliff | |
| 5,227,168 A * | 7/1993 | Chvapil et al. | 424/445 |
| 5,281,412 A | 1/1994 | Lukacovic | |
| 5,348,734 A | 9/1994 | Ratcliff | |
| 5,399,288 A | 3/1995 | Marzouk | |
| 5,407,656 A | 4/1995 | Roozdar | |
| 5,489,435 A | 2/1996 | Ratcliff | |
| 5,597,561 A | 1/1997 | Kross | |
| 5,618,550 A | 4/1997 | Ratcliff | |
| 5,651,996 A | 7/1997 | Roozdar | |
| 5,719,100 A | 2/1998 | Zahradnik | |
| 5,738,840 A | 4/1998 | Richter | |
| 5,820,822 A | 10/1998 | Kross | |
| 5,879,691 A | 3/1999 | Sagel | |
| 5,944,528 A | 8/1999 | Montgomery | |
| 5,980,923 A | 11/1999 | Dillon | |
| 6,007,735 A | 12/1999 | Creed | |
| 6,039,934 A | 3/2000 | Alliger | |
| 6,046,243 A | 4/2000 | Wellinghoff | |
| 6,077,495 A | 6/2000 | Speronello | |
| 6,077,502 A | 6/2000 | Witt | |
| 6,106,284 A | 8/2000 | Cronin | |
| 6,238,643 B1 * | 5/2001 | Thangaraj et al. | 423/477 |
| 6,280,716 B1 | 8/2001 | Ratcliff | |
| 6,280,775 B1 | 8/2001 | Sasson | |
| 6,287,551 B1 | 9/2001 | Ratcliff | |
| 6,294,108 B1 | 9/2001 | Speronello | |
| 6,294,510 B1 | 9/2001 | Norman | |
| 6,312,670 B1 | 11/2001 | Montgomery | |
| 6,379,658 B1 | 4/2002 | Marano | |
| 6,425,759 B1 | 7/2002 | Cronin | |
| 6,432,322 B1 | 8/2002 | Speronello | |
| 6,432,387 B1 | 8/2002 | Laizuka | |
| 6,479,037 B1 | 11/2002 | Montgomery | |
| 6,500,408 B2 | 12/2002 | Chen | |
| 6,551,579 B2 | 4/2003 | Sagel | |
| 6,582,682 B2 | 6/2003 | Stier | |
| 6,669,931 B2 | 12/2003 | Lynch | |
| 6,682,721 B2 | 1/2004 | Kim | |
| 6,699,404 B2 | 3/2004 | Speronello | |
| 6,759,030 B2 | 7/2004 | Kosti | |
| 6,848,905 B2 | 2/2005 | Jacobs | |
| 6,881,061 B2 | 4/2005 | Fisher | |
| 6,896,518 B2 | 5/2005 | Jacobs | |
| 6,964,571 B2 | 11/2005 | Andersen | |
| 7,004,756 B2 | 2/2006 | Andersen | |
| 7,029,705 B2 | 4/2006 | Fuhr | |
| 7,040,897 B2 | 5/2006 | Fischer | |
| 7,044,737 B2 | 5/2006 | Fu | |
| 7,087,190 B2 | 8/2006 | Hei | |
| 7,087,208 B2 | 8/2006 | Sampson | |
| 7,182,883 B2 | 2/2007 | Speronello | |
| 7,220,367 B2 | 5/2007 | Speronello | |
| 7,229,647 B2 | 6/2007 | Lee | |
| 7,273,567 B1 | 9/2007 | Wellinghoff | |
| 7,384,650 B2 | 6/2008 | Chien | |
| 7,514,019 B2 | 4/2009 | Martin | |
| 7,534,368 B2 | 5/2009 | Martin | |
| 7,875,460 B2 | 1/2011 | Ratcliff | |
| 2002/0137728 A1 | 9/2002 | Montgomery | |
| 2003/0152528 A1 | 8/2003 | Singh | |
| 2003/0235549 A1 | 12/2003 | Singh | |
| 2006/0024369 A1 | 2/2006 | Speronello | |
| 2006/0045855 A1 | 3/2006 | Sasson | |
| 2006/0088498 A1 | 4/2006 | Martin | |
| 2006/0099550 A1 | 5/2006 | Faasse | |
| 2006/0169949 A1 | 8/2006 | Speronello | |
| 2006/0183080 A1 | 8/2006 | Nosov | |
| 2006/0223033 A1 | 10/2006 | McLean | |
| 2006/0292090 A1 | 12/2006 | Sharma | |
| 2007/0172412 A1 | 7/2007 | Hratko | |
| 2007/0202095 A1 | 8/2007 | Speronello | |
| 2007/0231277 A1 | 10/2007 | Sharma | |
| 2007/0298380 A1 | 12/2007 | Allred | |
| 2008/0023668 A1 | 1/2008 | Callerame | |
| 2008/0025925 A1 | 1/2008 | Allred | |
| 2008/0041400 A1 | 2/2008 | Darnell | |
| 2008/0208179 A1 | 8/2008 | Chan | |
| 2008/0209650 A1 | 9/2008 | Brewer | |
| 2009/0016973 A1 | 1/2009 | Ratcliff | |
| 2009/0017548 A1 | 1/2009 | Ratcliff | |
| 2010/0009009 A1 | 1/2010 | Young | |
| 2010/0012891 A1 | 1/2010 | Speronello | |
| 2010/0012892 A1 | 1/2010 | Speronello | |
| 2010/0012893 A1 | 1/2010 | Speronello | |
| 2010/0012894 A1 | 1/2010 | Speronello | |
| 2010/0015066 A1 | 1/2010 | Speronello | |
| 2010/0015067 A1 | 1/2010 | Speronello | |
| 2010/0062042 A1 | 3/2010 | Speronello | |
| 2010/0062043 A1 | 3/2010 | Speronello | |
| 2010/0062076 A1 | 3/2010 | Speronello | |
| 2010/0074970 A1 | 3/2010 | Ratcliff | |
| 2010/0112059 A1 | 5/2010 | Speronello | |
| 2010/0221198 A1 | 9/2010 | Ratcliff | |
| 2010/0233101 A1 | 9/2010 | Grootveld | |
| 2011/0318282 A1 | 12/2011 | Ratcliff | |

FOREIGN PATENT DOCUMENTS

| | | |
|---|---|---|
| DE | 19854349 A1 | 5/2000 |
| JP | 60105610 | 6/1985 |
| WO | WO 2007/062347 A2 | 5/2007 |
| WO | WO 2007/079287 A2 | 7/2007 |
| WO | WO 2007/131970 A1 | 11/2007 |

OTHER PUBLICATIONS

Levy, et al., "Effect of Ultrasound on Transdermal Drug Delivery to Rats and Guinea Pigs," J. Clin. Invest., vol. 83, Jun. 1989, pp. 2074-2078.

* cited by examiner

CHLORINE DIOXIDE TREATMENT FOR BIOLOGICAL TISSUE

CROSS-REFERENCE TO RELATED APPLICATIONS

This application claims the benefit pursuant to 35 U.S.C. §119(e) of U.S. Provisional Application Nos. U.S. Provisional Application Nos. 61/149,784, filed Feb. 4, 2009; 61/150,685, filed Feb. 6, 2009; and 61/187,198, filed Jun. 15, 2009, each of which is hereby incorporated herein by reference in their entirety.

BACKGROUND

Chlorine dioxide is known to be a disinfectant, as well as a strong oxidizing agent. The bactericidal, algaecidal, fungicidal, bleaching, and deodorizing properties of chlorine dioxide are also well known. Therapeutic and cosmetic applications for chlorine dioxide are known. For example, U.S. Pat. No. 6,280,716 describes the use of stabilized chlorine dioxide solutions for the treatment of vaginal itching. U.S. Pat. No. 7,029,705 describes the use of stabilized chlorine dioxide solutions for a method of nasal hygiene.

The traditional method for preparing chlorine dioxide involves reacting sodium chlorite with gaseous chlorine ($Cl_2$ (g)), hypochlorous acid (HOCl), or hydrochloric acid (HCl). The reactions proceed at much greater rates in acidic medium, so substantially all traditional chlorine dioxide generation chemistry results in an acidic product solution having a pH below 3.5.

Chlorine dioxide may also be prepared from chlorate anion by either acidification or a combination of acidification and reduction. At ambient conditions, all reactions using chlorate anion require strongly acidic conditions; most commonly in the range of 7-9 N. Heating of the reagents to higher temperature and continuous removal of chlorine dioxide from the product solution can reduce the acidity needed to less than 1 N.

A method of preparing chlorine dioxide in situ uses a solution referred to as "stabilized chlorine dioxide." Stabilized chlorine dioxide solutions contain little or no chlorine dioxide, but rather, consist substantially of sodium chlorite at neutral or slightly alkaline pH. Addition of an acid to the sodium chlorite solution activates the sodium chlorite, and chlorine dioxide is generated in situ in the solution. The resulting solution is acidic. Typically, the extent of sodium chlorite conversion to chlorine dioxide is low, and a substantial quantity of sodium chlorite remains in the solution.

The current literature summarized above describes the use of chlorine dioxide compositions and methods that are damaging to biological tissues. Methods, compositions, devices, and systems for using chlorine dioxide for treatment of biological tissue in which biological tissue is not damaged are needed.

SUMMARY

The following embodiments meet and address these needs. The following summary is not an extensive overview. It is intended to neither identify key or critical elements of the various embodiments, not delineate the scope of them.

Provided is a method for treating a wound in a tissue comprising the step of administering to the wound a composition comprising a chlorine dioxide source to provide an efficacious amount of chlorine dioxide to the wound, thereby treating the wound. The administering step comprises one or more of: i) contacting the wound with a substantially non-cytotoxic and/or substantially non-irritating composition comprising the chlorine dioxide source; ii) contacting the wound with a device comprising the chlorine dioxide source and oxy-chlorine anions, wherein the device delivers a substantially oxy-chlorine anion free chlorine dioxide composition to the tissue; or iii) contacting the wound with a composition comprising the chlorine dioxide source and oxy-chlorine anions; and a barrier substance that substantially prohibits passage therethrough of the oxy-chlorine anions and permits passage therethrough of a substantially oxy-chlorine anion free chlorine dioxide composition, thereby enabling delivery of the substantially oxy-chlorine anion free chlorine dioxide composition to the wound.

In an embodiment, the method further comprises a second iteration of the contacting step, wherein the second iteration is substantially contiguous with the first iteration. In another embodiment, the method further comprises at least a third iteration of the contacting step, wherein the third iteration is substantially contiguous with the second iteration and the second iteration is substantially contiguous with the first iteration.

In some embodiments, the method comprises contacting the wound with a substantially non-cytotoxic and/or substantially non-irritating composition comprising the chlorine dioxide source to form a composition-contacted wound, and further comprising applying ultrasonic energy to the composition-contacted wound. In other embodiments, the administration step comprises contacting the wound with a device comprising the chlorine dioxide source and oxy-chlorine anions to form a device-contacted wound, and further comprising applying ultrasonic energy to the device-contacted wound. In certain embodiments, the ultrasonic energy frequency is between about 10 kHz to about 100 kHz with a power intensity of about 2 $W/cm^2$ to about 3.5 $W/cm^2$.

In other embodiments, the method comprises irrigating the wound with a substantially non-cytotoxic and/or substantially non-irritating composition using an irrigation device. In some embodiments, a substantially non-cytotoxic and/or substantially non-irritating composition comprises less than about 0.2 milligrams oxy-chlorine anion per gram composition. In yet other embodiments, the administration step comprises contacting the wound with a device comprising the chlorine dioxide source and oxy-chlorine anions, wherein the device is an irrigation device that delivers a substantially oxy-chlorine anion free chlorine dioxide composition to the wound.

In certain embodiments, the administration step comprises contacting the wound with a composition comprising the chlorine dioxide source and oxy-chlorine anions; and a barrier substance that substantially prohibits passage therethrough of the oxy-chlorine anions and permits passage therethrough of a substantially oxy-chlorine anion free chlorine dioxide composition, thereby enabling delivery of the substantially oxy-chlorine anion free chlorine dioxide composition to the wound to form a composition-contacted wound, and further comprising applying ultrasonic energy to the composition-contacted wound.

In some embodiments of the method of treating a wound in a tissue, the composition comprises about 1 to about 1000 ppm chlorine dioxide. In some embodiments, an actual dosage of at least about 200 ppm-minutes of chlorine dioxide is administered. In some embodiments, the chlorine dioxide source comprises chlorine-dioxide generating components, wherein said chlorine-dioxide generating components are particulate precursor of chlorine dioxide. Optionally, in any of the embodiments, the composition further comprises a second therapuetic agent. In other embodiments, the method further comprises administering a second composition comprising a second therapuetic agent to the wound.

In some embodiments, the method of treating a wound in a tissue comprises contacting the wound with a substantially non-cytotoxic and/or substantially non-irritating composition comprising the chlorine dioxide source, the composition comprising less than about 0.2 milligrams oxy-chlorine anion per gram composition. In other embodiments, the method of treating a wound in a tissue comprises the composition comprises a pH from about 4.5 to about 11.

Further provided is a system for irrigating a biological tissue, the system comprising: a device and a source of a fluid comprising chlorine dioxide. The irrigation device comprises: 1) a flexible, semi-rigid or rigid pouch or other containment chamber with inlet and outlet ports and with an opening to contact at least a portion of a tissue targeted to be irrigated; 2) a fluid supply and egress system connected to the chamber ports so as to provide fluid to or drain fluid from the chamber; 3) a means of maintaining contact of the chamber to the tissue which surrounds the target tissue so as to form a tight substantially leak-proof seal; 4) an optional open cell foam or other porous material placed inside the pouch to ensure a uniform distribution of flow; and 5) a fluid handling unit which supplies fluid to and/or allows fluid to exit the containment chamber, wherein the fluid handling unit supplies fluid from the source of the fluid comprising chlorine dioxide.

A method for alleviating an oral cavity tissue infection is also provided. The method comprises administering to infected tissue in an oral cavity a composition comprising a chlorine dioxide source to provide an efficacious amount of chlorine dioxide to the tissue, wherein the administering step comprises one or more of: i) contacting the tissue with a substantially non-cytotoxic and/or substantially non-irritating composition comprising the chlorine dioxide source to form a composition-contacted oral tissue, and applying ultrasonic energy to the composition-contacted oral tissue; ii) contacting the tissue iteratively with at least two, substantially contiguous applications of a substantially non-cytotoxic composition comprising the chlorine dioxide source; iii) irrigating the tissue with a substantially non-cytotoxic composition comprising the chlorine dioxide source using an irrigation device; or iv) irrigating the tissue using an irrigation device that delivers a substantially oxy-chlorine anion free chlorine dioxide composition to the wound.

In some embodiments, the composition comprising the chlorine dioxide source comprises about 1 to about 1000 ppm chlorine dioxide. In some embodiments, the composition comprising the chlorine dioxide source has a pH from about 4.5 to about 11. In some embodiments, the chlorine dioxide source comprises chlorine-dioxide generating components, wherein said chlorine-dioxide generating components are particulate precursor of chlorine dioxide. In some embodiments, the substantially non-cytotoxic and/or substantially non-irritating composition comprises less than about 0.2 milligrams oxy-chlorine anion per gram composition. Optionally, in any of the embodiments, the composition further comprises a second therapuetic agent. In other embodiments, the method further comprises administering a second composition comprising a second therapuetic agent to the infected oral cavity tissue.

In addition, a method of whitening a tooth surface is provided. The method comprises contacting a surface of a tooth with an efficacious amount of a composition comprising a chlorine dioxide source to provide an efficacious amount of chlorine dioxide to the tooth surface, wherein the contacting step comprises one or more of: i) contacting the tooth surface iteratively with at least two, substantially contiguous applications of a substantially non-cytotoxic and/or substantially non-irritating composition comprising a chlorine dioxide source; ii) irrigating the tooth surface using an irrigation device that delivers a substantially non-cytotoxic and/or substantially non-irritating composition comprising a chlorine dioxide source, or iii) irrigating the tooth surface using an irrigation device that delivers a substantially oxy-chlorine anion free chlorine dioxide composition to the tooth surface.

In some embodiments, the composition comprising the chlorine dioxide source comprises about 1 to about 1000 ppm chlorine dioxide. In some embodiments, the composition comprising the chlorine dioxide source has a pH from about 4.5 to about 11. In some embodiments, the chlorine dioxide source comprises chlorine-dioxide generating components, wherein said chlorine-dioxide generating components are particulate precursor of chlorine dioxide. In some embodiments wherein the contacting step comprises contacting the tooth surface iteratively with at least two, substantially contiguous applications of a substantially non-cytotoxic and/or substantially non-irritating composition comprising a chlorine dioxide source, each application comprises a chlorine dioxide dosage of about 750 ppm-minutes to about 2000 ppm-minutes. In some embodiments, at least four substantially contiguous applications are administered. In some embodiments, the substantially non-cytotoxic and/or substantially non-irritating composition comprises less than about 0.2 milligrams oxy-chlorine anion per gram composition.

BRIEF DESCRIPTION OF THE DRAWINGS

For the purpose of illustrating the various compositions and methods, there are depicted in the drawings certain embodiments of the methods, compositions, and devices disclosed. However, the compositions and their methods of use are not limited to the precise arrangements and instrumentalities of the embodiments depicted in the drawings.

FIG. 7 is a bar graph depicting the total log of coagulase-negative Staph in wounds after different delivery methods. The y-axis is log coagulase-negative Staph in (colony-forming units) per gram tissue. Moist control: data for wounds A1, B1, and D1. Irrigation pump: data for wounds A2-A4. NaCMC gel: data for wounds B2-B4. HPMC gel: data for wounds C2-C4. Irrigation syringe: data for wounds D2-D4. Manual irrigation: data for wound C1.

DETAILED DESCRIPTION

Figure 1:
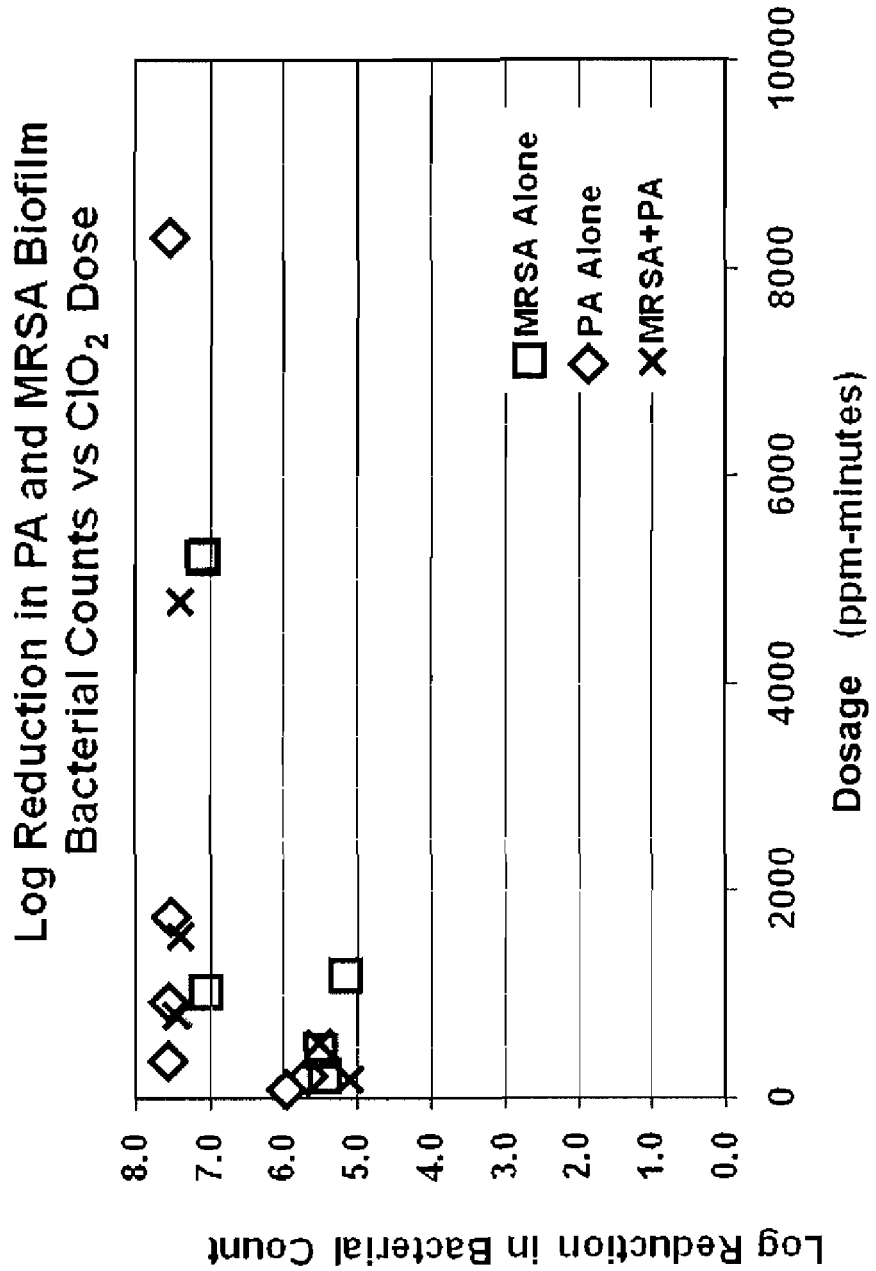
FIG. 1 is a graph depicting the reduction in log of bacteria (log kill) in various biofilms as a function of chlorine dioxide ($ClO_2$) dosage. MRSA=methicillin resistance *Staphylococcus aureus*. PA=*Pseudomonas aeruginosa*.

Provided herein are methods of delivering a chlorine-dioxide containing composition to a tissue or biological material. The methods are useful in the treatment of wounds, alleviation of an oral tissue infection and in tooth whitening.

Definitions

Unless defined otherwise, all technical and scientific terms used herein generally have the same meaning as commonly understood by one of ordinary skill in the art. Generally, the nomenclature used herein and the laboratory procedures in cytopathicity analysis, microbial analysis, organic and inorganic chemistry, and dental clinical research are those well known and commonly employed in the art.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it can be used. Generally, "about" encompasses a range of values that are plus/minus 10% of a reference value. For instance, "about 25%" encompasses values from 22.5% to 27.5%.

It is understood that any and all whole or partial integers between any ranges set forth herein are included herein.

As used herein, "biocidal" refers to the property of inactivating or killing pathogens, such as bacteria, algae, and fungi.

As used herein, "tooth whitening" refers to a lightening of tooth shade relative to the tooth shade prior to treatment. Lightening can be assessed on an isolated or an in situ tooth by standard, art-recognized methods of assessing tooth shade, which include qualitative, quantitative and semi-quantitative methods. For instance, lightening may be assessed by simple visual inspection, e.g., by comparing "before" and "after" photographs of the treated teeth. Alternatively, a tooth may be deemed whitened when the tooth shade relative to the tooth shade prior to treatment is two or more shades lighter, as assessed by Vita classical shade guide (typically under controlled visible light conditions) or two or more levels as assessed using the Vita Bleachedguide 3D-MASTER Shade system, which utilizes a multiple color spectrophotometer and includes half lightness levels. A difference of one shade is referred to herein as a "shade value unit" (SVU). Thus, for example, a difference of two shades is a 2 SVU difference.

"Bleaching agent" as used herein refers to the active ingredient, or combination of ingredients, in a composition that causes the lightening and/or removal of the chromagens that contribute to the dark shade of a tooth.

As used herein, a "biofilm" refers to a biological aggregate that forms a layer on a surface, the aggregate comprising a community of microorganisms embedded in an extracellular matrix of polymers. Typically, a biofilm comprises a diverse community of microorganisms, including bacteria (aerobic and anaerobic), algae, protozoa, and fungi. Monospecies biofilms also exist.

As used herein, an "efficacious amount" of an agent is intended to mean any amount of the agent that will result in a desired biocidal effect, a desired cosmetic effect, and/or a desired therapeutic biological effect. In one example, an efficacious amount of an agent used for tooth whitening is an amount that will result in whitening of a tooth with one or more treatments. In another example, an efficacious amount of an agent used for wound treatment is an amount that will result in a statistically significant improvement in wound healing such as a reduction in bacterial level in the wound.

As used herein, a "wound" refers to a laceration, abrasion, puncture, burn, and/or other injury to any one or more soft and/or hard tissue. Exemplary tissues considered for such wound treatment include mucosal tissue and dermal tissue including epidermal tissue, dermal tissue, and subcutaneous tissue (also called hypodermis tissue). As used herein, a wound also encompasses a laceration, a puncture, and/or an avulsion of a fingernail or toenail. A wound can penetrate the tissue partially or completely. A wound can arise accidently or intentionally, e.g., a surgical wound.

As used herein, a wound is "treated" if one or more indications of wound healing are improved to a statistically significant amount or degree. Indications of wound healing are well known in the art. Indications of wound healing can be present in any one or more of the four general overlapping phases of wound healing: hemostasis phase, inflammatory phase, proliferative phase, and remodeling phase, and include the extent or the duration of each phase or of the overall healing process. Other examples of indications of wound healing include reduction in total bacterial count, reduction in bacterial count of a specific bacteria such as *Pseudomonas aeruginosa* or Staphylococci, reduction in extent or duration of inflammation, increase in extent of or rate of wound contraction, reduction in overall time to healing, and the like.

As used herein, "biological tissue" refers to soft biological tissue and hard biological tissue.

As used herein, a "soft biological tissue" refers to mucosal tissue and dermal tissue. Dermal tissue encompasses epidermal tissue, dermal tissue, and subcutaneous tissue (also called hypodermis tissue). "Soft tissue" is used herein interchangeably with "soft biological tissue."

As used herein, "hard biological tissue" refers to toe and finger nails, hard keratinized tissues, hard tooth tissue, and the like, found in animals such as mammals. "Hard tissue" is used herein interchangeably with "hard biological tissue."

As used herein, "hard tooth tissue" refers to at least one of enamel and dentin.

As used herein, "hard tooth tissue damage" refers to at least one of a reduction of microhardness of enamel, a reduction of microhardness of dentin, an increase in the surface roughness of enamel and an increase in the surface roughness of dentin.

As used herein, a composition "does not substantially damage hard tooth tissue" if one or more of the following is met for a tooth after treatment relative to the tooth prior to treatment: 1) enamel microhardness is decreased by an amount less than about 15% and/or the reduction is not statistically significant at the 5% confidence level; 2) dentin microhardness is decreased by an amount less than about 15% and/or the reduction is not statistically significant at the 5% confidence level; 3) enamel surface roughness is increased by an amount no more than about 20% and/or the increase is not statistically significant at the 5% confidence level; and 4) dentin surface roughness is increased by an amount no more than about 8% and/or the increase is not statistically significant at the 5% confidence level.

As used herein, "remineralization" refers to the process of repair of acid damaged tooth structure by the recrystallization of mineral salts on or within the tooth architecture.

As used herein, "demineralization" refers to the process of mineral loss from teeth caused by acid, chelating agents or other accelerants of dissolution. Demineralization can occur on tooth surfaces and/or below tooth surfaces, depending on the composition of the demineralizing agent, the contacting medium, the concentration, and the pH.

As used herein, "irrigation" of a tissue refers to rinsing the tissue with a solution. "Continuous irrigation" refers to rinsing the tissue with a substantially steady stream of the solution for the duration of the treatment. "Intermittent irrigation" refers to rinsing the tissue with a stream of fluid that is periodically slowed or stopped during the treatment.

As used herein, a "plurality" refers to two or more. For instance, a treatment having a plurality of contacting steps encompasses two, three, four, five, six, seven, eight or more steps of contacting.

As used herein, a "chlorine dioxide source" refers to one of chlorine dioxide, chlorine dioxide-generating components, or a combination of thereof.

As used herein, an "oral cavity infection" refers to a disease or disorder of a tissue in an oral cavity caused by a pathogenic infection. The pathogen may be bacterial, viral, or fungal. An oral disease encompasses conditions wherein if the disease is not ameliorated then the animal's oral health continues to deteriorate. In contrast, an oral disorder is a state of oral health in which the animal is able to maintain homeostasis, but in which the animal's state of health is less favorable than it would be in the absence of the disorder. Left untreated, a disorder does not necessarily cause a further decrease in the animal's state of oral health. The term encompasses periodontal disease, halitosis, thrush, and dental caries development.

As used herein, a "periodontal disease" is an infection of the tissues that support a subject's teeth, caused by a pathogenic infection. Periodontal disease includes gingivitis and periodontitis.

As used herein, "dental plaque" refers to a biofilm that forms on the surface of teeth.

As used herein, a disease or disorder is "alleviated" if the severity of a symptom of the disease or disorder, the frequency with which such a symptom is experienced by a patient, or both, are reduced.

A "therapeutic" treatment is a treatment administered to a subject who exhibits signs of pathology for the purpose of diminishing or eliminating those signs.

A "prophylactic" treatment is a treatment administered to a subject who does not exhibit signs of a disease or exhibits early signs of the disease for the purpose of decreasing the risk of developing pathology associated with the disease.

As used herein, "cytotoxic" refers to the property of causing lethal damage to mammalian cell structure or function. A composition is deemed "substantially non-cytotoxic" or "not substantially cytotoxic" if the composition meets the United States Pharmacopeia (USP) biological reactivity limits of the Agar Diffusion Test of USP <87> "Biological Reactivity, in vitro," (approved protocol current in 2007) when the active pharmaceutical ingredient (API) is present in an efficacious amount.

As used herein, "irritating" refers to the property of causing a local inflammatory response, such as reddening, swelling, itching, burning, or blistering, by immediate, prolonged, or repeated contact. For example, inflammation of a non-oral mucosal or dermal tissue in a mammal can be an indication of irritation to that tissue. A composition is deemed "substantially non-irritating" or "not substantially irritating," if the composition is judged to be slightly or not irritating using any standard method for assessing dermal or mucosal irritation. Non-limiting examples of methods useful for assessing dermal irritation include the use of in vitro tests using tissue-engineered dermal tissue, such as EpiDerm™ (MatTek Corp., Ashland, Mass.), which is a human skin tissue model (see, for instance, Chatterjee et al., 2006, *Toxicol Letters* 167: 85-94) or ex vivo dermis samples. Non-limiting examples of methods useful for mucosal irritation include: HET-CAM (hen's egg test-chorioallantoic membrane); slug mucosal irritation test; and in vitro tests using tissue-engineered nasal or sinus mucosa or vaginal-ectocervical tissues. Other useful methods of irritation measurement include in vivo methods, such as dermal irritation of rat or rabbit skin (e.g., the Draize skin test (OECD, 2002, Test Guidelines 404, Acute Dermal Irritation/Corrosion) and EPA Health Effects Testing Guidelines; OPPTS 870.2500 Acute Dermal Irritation). The skilled artisan is familiar with art-recognized methods of assessing dermal and mucosal irritation.

As used herein, "oxy-chlorine anion" refers to chlorite ($ClO_2$) and/or chlorate ($ClO_3^-$) anions.

As used herein, "substantially pure chlorine dioxide solution" refers to a solution of chlorine dioxide that has a non-cytotoxic concentration of oxy-chlorine anion. As used herein, "substantially pure chlorine dioxide solution" also refers to a concentrated solution of chlorine dioxide that contains a concentration of oxy-chlorine anion that upon dilution to an efficacious amount of chlorine dioxide is not cytotoxic with respect to the concentration of oxy-chlorine anion.

By "substantially oxy-chlorine anion free chlorine dioxide composition" is meant a composition that contains an efficacious amount of chlorine dioxide and a non-cytotoxic and/or non-irritating concentration of oxychlorine anion, all as defined hereinabove. The composition may contain other components or may consist essentially of oxy-chlorine anion free chlorine dioxide. The composition may be a gas or vapor comprising or consisting essentially of chlorine dioxide, but may be any type of fluid, including a solution or a thickened fluid. The composition may be an aqueous fluid or a non-aqueous fluid.

By "stable" is meant that the components used to form chlorine dioxide, i.e., the chlorine dioxide forming ingredients, are not immediately reactive with each other to form chlorine dioxide. It will be understood that the components may be combined in any fashion, such as sequentially and/or simultaneously, so long as the combination is stable until such time that $ClO_2$ is to be generated.

By "non-reactive" is meant that a component or ingredient as used is not immediately reactive to an unacceptable degree with other components or ingredients present to form chlorine dioxide or mitigate the ability of any component or ingredient to perform its function in the formulation at the necessary time. As the skilled artisan will recognize, the acceptable timeframe for non-reactivity will depend upon a number of factors, including how the formulation is to be formulated and stored, how long it is to be stored, and how the formulation is to be used. Accordingly, "not immediately reactive" will range from one or more minutes, to one or more hours, to one or more weeks.

The phrase "thickened fluid composition" encompasses compositions which can flow under applied shear stress and which have an apparent viscosity when flowing that is greater than the viscosity of the corresponding aqueous chlorine dioxide solution of the same concentration. This encompasses the full spectrum of thickened fluid compositions, including: fluids that exhibit Newtonian flow (where the ratio of shear rate to shear stress is constant and viscosity is independent of shear stress), thixotropic fluids (which require a minimum yield stress to be overcome prior to flow, and which also exhibit shear thinning with sustained shear), pseudoplastic and plastic fluids (which require a minimum yield stress to be overcome prior to flow), dilantant fluid compositions (which increase in apparent viscosity with increasing shear rate), and other materials which can flow under applied yield stress.

A "thickener component," as the phrase is used herein, refers to a component that has the property of thickening a solution or mixture to which it is added. A "thickener component" can be used to make a "thickened fluid composition" as described above.

By "apparent viscosity" is meant the ratio of shear stress to shear rate at any set of shear conditions that result in flow. Apparent viscosity is independent of shear stress for Newtonian fluids and varies with shear rate for non-Newtonian fluid compositions.

The term "particulate" is defined to mean all solid materials. By way of a non-limiting example, particulates may be interspersed with each other to contact one another in some way. These solid materials include particles comprising big particles, small particles or a combination of both big and small particles.

As used herein, "NaDCCA" refers to sodium dichloroisocyanurate and/or the dihydrate thereof.

By "source of free halogen" and "free halogen source" is meant a compound or mixtures of compounds which release halogen upon reaction with water.

By "free halogen" is meant halogen as released by a free halogen source.

By "particulate precursor of chlorine dioxide" is meant a mixture of chlorine-dioxide-forming components that are particulate. Granules of ASEPTROL (BASF, Florham Park, N.J.) are an exemplary particulate precursor of chlorine dioxide.

By "solid body" is meant a solid shape, typically a porous solid shape, or a tablet comprising a mixture of granular particulate ingredients wherein the size of the particulate ingredients is substantially smaller than the size of the solid body; by "substantially smaller" is meant at least 50% of the particles have a particle size at least one order of magnitude, and preferably at least two orders of magnitude, smaller than the size of solid body.

The term "hydrophobic" or "water-insoluble," as used with respect to organic polymers refers to an organic polymer, which has a water solubility of less than about one gram per 100 grams of water at 25° C.

By "acid source" is meant a material, usually a particulate solid material, which is itself acidic or produces an acidic environment when in contact with liquid water or solid oxychlorine anion.

A "matrix," as used herein, is a material that functions as a protective carrier of chlorine dioxide-generating components. A matrix is typically a continuous solid or fluid phase in which the materials that can participate in a reaction to form chlorine dioxide are suspended or otherwise contained. The matrix can provide physical shape for the material. If sufficiently hydrophobic, a matrix may protect the materials within from contact with moisture. If sufficiently rigid, a matrix may be formed into a structural member. If sufficiently fluid, a matrix may function as a vehicle to transport the material within the matrix. If sufficiently adhesive, the matrix can provide a means to adhere the material to an inclined or vertical, or horizontal downward surface. A fluid matrix may be a liquid such that it flows immediately upon application of a shear stress, or it may require that a yield stress threshold be exceeded to cause flow. In some embodiments, the matrix can be either a fluid, or capable of becoming fluid (e.g., upon heating) such that other components may be combined with and into the matrix (e.g., to initiate reaction to form chlorine dioxide). In other embodiments, the matrix is a continuous solid; chlorine dioxide generation can be initiated by, for instance, penetration of water or water vapor, or by light activation of an energy-activatable catalyst.

By "film" is meant a layer of a material having two dimensions substantially larger than the third dimension. A film may be a liquid or a solid material. For some materials, a liquid film can be converted into a solid film by curing, for instance, by evaporation, heating, drying and/or cross-linking.

Unless otherwise indicated or evident from context, preferences indicated above and herein apply to the entirety of the embodiments discussed herein.

Description

Disclosed are methods of delivering chlorine dioxide to a tissue, such as a wound, infected oral tissue, or hard biological tissue such as a tooth surface. The methods can be practiced on the tissue of any animal. Non-limiting examples of animals are mammals, such as humans, non-human primates, domesticated animals such as cattle, horses, dogs, sheep, goats, and pigs, and rodents such as mice and rats. In an embodiment, the methods are practiced on a human tissue.

Chlorine dioxide has well-documented potent biocidal activity. Disadvantageously, chlorine dioxide-containing compositions of the prior art can be cytotoxic and irritating to soft tissues such as mucosal tissue or dermal tissue, and damaging to hard tissues such as hard tooth tissue. The cytotoxicity of chlorine dioxide-containing compositions results predominantly from the presence of oxy-chlorine anions, and not from the presence of chlorine, which can be a product of chlorine dioxide decomposition. By substantially preventing or inhibiting oxy-chlorine anions present in a chlorine-dioxide containing composition from contacting cells and tissues, including hard tooth tissues such as enamel and dentin and soft tissues, such as wound tissue or oral mucosa and gums, that are targeted for treatment, tissue damage can be measurably reduced or minimized, while achieving the biocidal efficacy or bleaching efficacy of chlorine dioxide.

As shown herein, chlorine dioxide is efficacious in disrupting, penetrating and/or otherwise inactivating biofilms on surfaces, including biofilms of methicillin resistant *Staphylococcus aureus* (MRSA), *Pseudomonas aeruginosa* (PA) or a combination thereof. MRSA is a resistant variation of the common bacterium *Staphylococcus aureus*. It has evolved an ability to survive treatment with beta-lactamase-resistant beta-lactam antibiotics, including methicillin, dicloxacillin, nafcillin, and oxacillin. PA is an opportunistic pathogen with a low intrinsic antibiotic sensitivity and the capacity to readily acquire antibiotic resistance. PA has emerged as a nosocomial pathogen of increasing clinical relevance. It is demonstrated herein that chlorine dioxide is efficacious in disrupting, penetrating, and/or otherwise inactivating biofilms, even in the presence of a protein-rich environment. As further shown herein, administration of chlorine dioxide to a wound in accordance with the methods described can reduce total bacterial log count in the wound. It is, further demonstrated that one can estimate the effect of blood serum in a wound on the rate of consumption of chlorine dioxide, therefore one can estimate dosage (in ppm-min) for efficacy with more accuracy. It is also shown herein that altering the specific treatment regimen of treating a tooth surface with a chlorine dioxide composition can affect the extent of tooth whitening for a given dosage (in ppm-min) to a statistically significant amount.

Accordingly, the methods described herein generally pertain to the administration of a composition comprising a chlorine dioxide source to a wound in a substantially non-cytotoxic and/or non-irritating manner to treat the wound.

A wound refers to a laceration, abrasion, puncture or other injury to one or more tissues. The tissue can be any of mucosal tissue, dermal tissue including epidermal tissue, dermal tissue, and subcutaneous tissue (also called hypodermis tissue), and hard tissue such as fingernail and toenail. A wound can penetrate the tissue partially or completely. A wound can arise via accidental trauma or intentionally, e.g., a surgical wound. Wounds range from acute to chronic. Acute wounds heal in an orderly set of stages and in a relatively sort period of time. Chronic wounds are wounds of long duration, e.g., greater than 3 months, that heal very slowly. The most common chronic wounds are venous ulcers, diabetic ulcers and pressure ulcers. Bacterial colonization is a problem in both acute wounds and chronic wounds. The immune response to bacterial colonization can prolong wound inflammation, delay healing and cause tissue damage. Bacterial colonization characterized by the presence of biofilm is particularly difficult to treat adequately with the therapetics currently available. As shown herein, chlorine dioxide is a robust agent for disrupting, penetrating and/or otherwise inactivating biofilm, even in the presence of a protein-rich environments such as the exudate present in a wound bed.

In some embodiments, the method of treating a wound comprises contacting the tissue with a substantially non-cytotoxic and/or non-irritating composition. In other embodiments, the method comprises contacting the wound with a device or composition that delivers a substantially oxy-chlorine anion free chlorine dioxide composition to the wound. In yet other embodiments, contact comprises irrigation of the wound tissue. In some embodiments, a combination therapy is carried out, such as including a step of improving tissue penetration of chlorine dioxide, for instance by use of ultrasonic energy.

The methods described herein also generally pertain to the administration of a composition comprising chlorine dioxide to a tissue in a substantially non-cytotoxic and/or non-irritating manner to alleviate an infection of an oral tissue.

The methods described herein are useful in the treatment of any infection of any oral cavity tissue susceptible to topical exposure of a biocidal agent, in particular, chlorine dioxide. Infections of oral cavity tissue include, but are not limited to, halitosis, gingivitis, periodontitis, caries formation, and thrush. Oral tissue may be intact or may have one or more incisions, lacerations or other tissue-penetrating opening. The methods may be practiced prophylactically or therapeutically.

Bacteria in the oral cavity can produce volatile sulfur compounds (VSCs) which underlie oral malodor or halitosis. VSCs include hydrogen sulfide, methylmercaptan and dimethylmercaptan. Exemplary bacteria that can contribute to this problem include: *Fusobacterium nucleatum, Treponema denticola, Tannerella forsythia* (formerly *Bacteroides forsythus*), *Prevotella intermedia, Porphyromonas gingivalis, Porphyromonas endodontalis*, and *Eubacterium* species.

Dental plaque is a biofilm that forms on the surface of teeth. Oral cavity infections that are related to dental plaque include caries development, gingivitis, and periodontitis. While hundreds of bacteria have been detected in dental plaque, the most common bacteria that contribute to gingivitis and periodontitis are: *Actinobacillus actinomycetemcomitans, Campylobacter rectus, Eikenella corrodens* and seven anaerobic species, *Porphyromonas gingivalis, Bacteroides forsythus, Treponema denticola, Prevotella intermedia, Fusobacterium nucleatum, Eubacterium*, and spirochetes. *P. gingivalis*, a gram-negative anaerobe, is believed to be largely responsible for adult periodontitis. Various herpes viruses have also been found to contribute to destructive periodontal disease. The bacteria that largely underlie caries formation are *Streptococcus mutans, Lactobacillus acidophilus, Actinomyces viscosus*, and *Nocardia* spp.

Oral thrush is the most common oral fungal infection. The causative agents of oral thrush are *Candida albicans* and *Candida dubliniensis*. *C. dubliniensis* is typically found in immunocompromised patients, such as AIDS patients, organ transplant patients and patients undergoing chemotherapy.

Oral cavity infections such as gingivitis, periodontitis and caries are quite difficult to treat since, in many cases, the bacteria responsible for the infection are in biofilm form and located in difficult to reach supra- and (even more difficult to reach) sub-gingival pockets. Periodontitis an inflammatory disease affecting the tissues that surround and support the teeth. The microorganism causing periodontitis adheres to and grows on the tooth's surfaces, and there is an overly aggressive immune response against these microorganisms. Periodontitis involves progressive loss of the alveolar bone around the teeth, and, if left untreated, can lead to the loosening and subsequent loss of teeth. Standard treatment often involves root planning and scaling, which is uncomfortable for the patient and often requires an analgesic be administered. In some cases, invasive surgery is necessary to treat periodontitis. Current treatment often includes an antimicrobial mouth wash having chlorhexidine as the antimicrobial. Chlorhexidine can have the undesirable side effect of staining teeth.

Thus, a method for alleviating infected oral cavity tissue is provided. The methods provided are contemplated as improving contact between chlorine dioxide and the reservoirs of biofilm located in supra- and sub-gingival pockets. Administration to the oral cavity can take the form of continuous irrigation, intermittent irrigation (e.g., rinsing or washing), multiple substantially contiguous applications, combination therapy to improve tissue penetration, use of dental trays designed to deliver content to the gingival pockets, and direct tissue injection of chlorine dioxide compositions such as gels or solutions. In some embodiments, a combination therapy is carried out, that includes a step of improving oral mucosal tissue penetration of chlorine dioxide, for instance by use of ultrasonic energy.

The methods described herein further generally pertain to the administration of a composition comprising chlorine dioxide to a tooth surface in a substantially non-cytotoxic and/or non-irritating manner to whiten the tooth surface.

The normal shade of teeth is determined by the natural off-white tints of the enamel and the dentin beneath. Extrinsic and intrinsic staining also contribute to tooth color. Extrinsic staining refers to surface stains, such as those caused by tea, coffee, red wine, and other foods rich in polyphones. Extrinsic stains can be removed through the use of surfactants and/or abrasives, which cause their physical removal from the tooth surface.

Intrinsic staining refers to stains that exist below enamel surface, or that penetrate below enamel surface. Intrinsic staining can happen when food molecules seep into enamel flaws and cracks, or, in some cases, between enamel rods. Intrinsic discoloration can also occur following a change to the structural composition or thickness of the dental hard tissues. Removal of intrinsic staining is more difficult and time consuming than removal of extrinsic staining. Intrinsic stain removal can be achieved by a variety of methods including use of peroxides or peroxide analogs, with or without chemical, light or heat activation, to bleach the stains. Among the side effects associated with the use of peroxides are tooth sensitivity, soft tissue irritation (e.g., gingival irritation) and tooth surface changes (e.g., changes to dentin and/or enamel).

Tooth whitening using substantially non-cytotoxic and/or substantially non-irritating chlorine dioxide-containing compositions has been shown to be efficacious in whitening and characterized by reduced soft tissue irritation and reduced changes to enamel and dentin of teeth. See commonly-assigned U.S. application Ser. Nos. 12/502,761, 12/502,781, 12/502,895, 12/502,907, and 12/502,925, filed Jul. 14, 2009.

The methods described herein can provide statistically significantly improved tooth whitening. In an embodiment, the method for whitening a tooth surface comprises at least two iterations of a step of contacting the tooth surface with a composition comprising a chlorine dioxide source, wherein the iterations are substantially contiguous. In an embodiment, each iteration uses a fresh specimen of the composition. By "fresh specimen" is meant a specimen of composition that has not been previously exposed to a biological tissue. In one aspect, the contacting step comprises contacting the tooth surface with a substantially non-cytotoxic and/or non-irritating composition. In another aspect, the contacting step comprises irrigating the tooth surface using an irrigation device. The irrigation device can deliver a substantially non-cytotoxic and/or non-irritating fluid composition. Alternatively, the irrigation device can be modified so as to deliver a substantially oxy-chlorine anion free chlorine dioxide composition.

I. Chlorine Dioxide-Generating Components

The methods employ a composition that comprises a chlorine dioxide source. A chlorine dioxide source refers to chlorine dioxide, chlorine dioxide-generating components, and combinations thereof. Chlorine dioxide-generating components refer to at least an oxy-chlorine anion source and an activator of chlorine dioxide generation. In some embodiments, the activator is an acid source. In these embodiments, the components optionally further includes a free halogen source. The free halogen source may be a cationic halogen source, such as chlorine. In other embodiments, the activator is an energy-activatable catalyst. In yet other embodiments, the activator is a dry or anhydrous polar material. In other embodiments, the activator is an aqueous fluid such as water, saliva, mucus, and wound exudate, and/or water vapor.

Oxy-chlorine anion sources generally include chlorites and chlorates. The oxy-chlorine anion source may be an alkali metal chlorite salt, an alkaline earth metal chlorite salt, an alkali metal chlorate salt, an alkaline earth metal chlorate salt and combinations of such salts. In exemplary embodiments, the oxy-chlorine anion source is a metal chlorite. In some embodiments, the metal chlorite is an alkali metal chlorite, such as sodium chlorite and potassium chlorite. Alkaline earth metal chlorites can also be employed. Examples of alkaline earth metal chlorites include barium chlorite, calcium chlorite, and magnesium chlorite. An exemplary metal chlorite is sodium chlorite.

For chlorine dioxide generation activated by an acid source, the acid source may include inorganic acid salts, salts comprising the anions of strong acids and cations of weak bases, acids that can liberate protons into solution when contacted with water, organic acids, inorganic acids, and mixtures thereof. In some aspects, the acid source is a particulate solid material which does not react substantially with the metal chlorite during dry storage, however, does react with the metal chlorite to form chlorine dioxide when in the presence of an aqueous medium. The acid source may be water soluble, substantially insoluble in water, or intermediate between the two. Exemplary acid sources are those which produce a pH of below about 7, more preferably below about 5.

Exemplary substantially water-soluble, acid-source-forming components include, but are not limited to, water-soluble solid acids such as boric acid, citric acid, tartaric acid, water soluble organic acid anhydrides such as maleic anhydride, and water soluble acid salts such as calcium chloride, magnesium chloride, magnesium nitrate, lithium chloride, magnesium sulfate, aluminum sulfate, sodium acid sulfate ($NaHSO_4$), sodium dihydrogen phosphate ($NaH_2PO_4$), potassium acid sulfate ($KHSO_4$), potassium dihydrogen phosphate ($KH_2PO_4$), and mixtures thereof. Exemplary acid-source-forming component is sodium acid sulfate (sodium bisulfate). Additional water-soluble, acid-source-forming components will be known to those skilled in the art.

Chlorine dioxide-generating components optionally comprise a source of free halogen. In one embodiment, the free halogen source is a free chlorine source, and the free halogen is free chlorine. Suitable examples of free halogen source used in the anhydrous compositions include dichloroisocyanuric acid and salts thereof such as NaDCCA, trichlorocyanuric acid, salts of hypochlorous acid such as sodium, potassium and calcium hypochlorite, bromochlorodimethylhydantoin, dibromodimethylhydantoin and the like. An exemplary source of free halogen is NaDCCA.

For chlorine dioxide generation activated by an energy-activatable catalyst, the energy-activatable catalyst can be selected from the group consisting of a metal oxide, a metal sulfide, and a metal phosphide. Exemplary energy-activatable catalysts include metal oxides selected from the group consisting of titanium dioxide ($TiO_2$); zinc oxide (ZnO); tungsten trioxide ($WO_3$); ruthenium dioxide ($RuO_2$); iridium dioxide ($IrO_2$); tin dioxide ($SnO_2$); strontium titanate ($SrTiO_3$); barium titanate ($BaTiO_3$); tantalum oxide ($Ta_2O_5$); calcium titanate ($CaTiO_3$); iron (III) oxide ($Fe_2O_3$); molybdenum trioxide ($MoO_3$); niobium pentoxide ($NbO_5$); indium trioxide ($In_2O_3$); cadmium oxide (CdO); hafnium oxide ($HfO_2$); zirconium oxide ($ZrO_2$); manganese dioxide ($MnO_2$); copper oxide ($Cu_2O$); vanadium pentoxide ($V_2O_5$); chromium trioxide ($CrO_3$); yttrium trioxide ($YO_3$); silver oxide ($Ag_2O$), $Ti_xZr_{1-x}O_2$, wherein x is between 0 and 1, and combinations thereof. The energy-activatable catalyst can be selected from the group consisting of titanium oxide, zinc oxide, calcium titanate, zirconium oxide and combinations thereof.

Chlorine dioxide-generating components optionally may be present in a matrix. Such matrices may be organic matrices, such as those described in commonly-assigned U.S. Pat. Publication No. 2006/0024369. In these matrices, chlorine dioxide is generated when the composite is exposed to water vapor or electromagnetic energy. The matrix may be a hydrous gel or an anhydrous gel. Hydrophobic matrices may also be employed. Hydrophobic matrix materials include water-impervious solid components such as hydrophobic waxes, water-impervious fluids such as hydrophobic oils, and mixtures of hydrophobic solids and hydrophobic fluids. In embodiments using a hydrophobic matrix, activation of chlorine dioxide may be a dry or anhydrous polar material, as described in co-pending U.S. Application No. 61/153,847.

II. Delivery Methods

1. Non-Cytotoxic/Non-Irritating Composition

In an embodiment, the method comprises contacting a wound, tooth surface, or an oral cavity with a substantially non-cytotoxic and/or substantially non-irritating composition comprising a chlorine dioxide source.

For compositions comprising an oxidizing or bleaching agent consisting of chlorine dioxide, cytotoxicity results predominantly from the presence of oxy-chlorine anions, absent other constituents that contribute to cytotoxicity. Accordingly, a composition comprising chlorine dioxide that comprises zero milligram (mg) oxy-chlorine anion per gram composition to no more than about 0.25 mg oxy-chlorine anion per gram composition, from zero to about 0.24, 0.23, 0.22, 0.21, or 0.20 mg oxy-chlorine anion per gram composition, from zero to 0.19, 0.18, 0.17, 0.16, 0.15, 0.14, 0.13, 0.12, 0.11, or 0.10 mg oxy-chlorine anion per gram composition or from zero to 0.09, 0.08, 0.07, 0.06, 0.05 or 0.04 mg oxy-chlorine anion per gram composition, absent other constituents that contribute to cytotoxicity, is substantially non-cytotoxic.

Oxy-chlorine anions can be measured in chlorine dioxide solutions or compositions using any method known to those skilled in the art, including ion chromatography following the general procedures of EPA test method 300 (Pfaff, 1993, "Method 300.0 Determination of Inorganic Anions by Ion Chromatography," Rev. 2.1, US Environmental Protection Agency) or a titration method based on an amperometric method (Amperometric Method II in Eaton et al, ed., "Standard Methods for the Examination of Water and Wastewater" 19$^{th}$ edition, American Public Health Association, Washington D.C., 1995). Alternatively, oxy-chlorine anions may be measured by a titration technique equivalent to the amperometric method, but which uses the oxidation of iodide to iodine and subsequent titration with sodium thiosulfate to a starch endpoint in place of the amperometric titration; this method is referred to herein as "pH 7 buffered titration." A chlorite analytical standard can be prepared from technical grade solid sodium chlorite, which is generally assumed to comprise about 80% by weight of pure sodium chlorite.

Soft tissue irritation can result from highly reactive oxygen species and/or extremes of pH, both acidic and basic. To minimize soft tissue irritation by the chlorine dioxide containing composition, the substantially non-cytotoxic composition has a pH of at least 3.5. Preferably, the composition has a pH of at least 5, and more preferably still, greater than about 6. In certain embodiments, the pH ranges from about 4.5 to about 11, more preferably from about 5 to about 9, and more preferably still, greater than about 6 and less than about 8. In one embodiment, the pH is about 6.5 to about 7.5. The concentration of oxy-chlorine anions is not believed to be a primary contributor to soft tissue irritation.

Methods of preparing non-cytotoxic and/or non-irritating compositions comprising chlorine dioxide are described in commonly-assigned U.S. application Ser. Nos. 12/502,761 and 12/502,781, filed Jul. 14, 2009, entitled "Tooth Whitening Compositions and Methods," and U.S. application Ser. Nos. 12/502,326 and 12/502,356, filed Jul. 14, 2009, entitled "Non-Cytotoxic Chlorine Dioxide Fluids," each of which is incorporated herein by reference in its entirety.

In an embodiment, a substantially non-cytotoxic composition comprising chlorine dioxide can be prepared using a substantially pure chlorine dioxide solution having a neutral pH. In some embodiments, the substantially pure chlorine dioxide solution has a pH from about 5 to about 9, and more preferably, from about 6.5 to about 7.5.

Substantially pure chlorine dioxide may be prepared by preparing a chlorine dioxide solution using any known method, then bubbling a gas (e.g., air) through that solution (sparging) and into a second container of deionized water, to prepare the product solution of substantially pure chlorine dioxide. Only $ClO_2$ and possibly some water vapor are transferred from the source solution to the product solution. All the salt ingredients and acid remain behind in the source solution. Thus, there are no oxy-chlorine anions in the substantially pure product solution. One method of preparing chlorine dioxide comprises combining an aqueous solution of sodium chlorite with a mineral acid to reduce the solution pH to below about 3.5 and allowing the solution to react for a sufficient time, e.g., about 30 minutes, to generate chlorine dioxide. The resulting solution is then sparged, as described above, to prepare the product solution of substantially pure chlorine dioxide.

While the substantially pure chlorine dioxide may undergo a degree of decomposition, the rate is relatively slow. By keeping the solution capped and protected from ultraviolet exposure, the decomposition rate can be slowed to a rate of about 5% to about 25% reduction in chlorine dioxide in 7 days. Substantially pure chlorine dioxide may also be prepared using a pervaporation technique, such as that disclosed in U.S. Pat. No. 4,683,039. In addition, a metal chlorite and an acid source can be reacted in solution to yield high conversion to chlorine dioxide and produce a greater than 2000 ppm chlorine dioxide solution. The concentrated solution can then be buffered to a neutral pH. Similarly, a chlorine dioxide solution can be prepared using the composition described in U.S. Pat. No. 5,399,288, which yields a high concentration chlorine dioxide solution at acidic pH. The concentrated solution can then be buffered to achieve a substantially neutral pH to prepare a substantially pure chlorine dioxide solution.

Another source of a substantially pure chlorine dioxide solution is chlorine dioxide is prepared using an ASEPTROL (BASF Corp., Florham Park, N.J.) material, which are described in commonly-assigned U.S. Pat. Nos. 6,432,322 and 6,699,404. These patents disclose substantially anhydrous solid bodies comprising particulate components for preparing highly-converted solutions of chlorine dioxide when added to water. The particulate components in the solid bodies comprise a metal chlorite such as sodium chlorite, an acid source such as sodium bisulfate and optionally a source of free halogen such as the sodium salt of dichloroisocyanuric acid or a hydrate thereof (collectively referred to herein as "NaDCCA"). Chlorine dioxide is generated when an ASEPTROL material is contacted with water or an aqueous medium. ASEPTROL material can be made to have an extremely high conversion rate in an aqueous solution, as described in U.S. Pat. Nos. 6,432,322 and 6,699,404, resulting in high concentrations of chlorine dioxide and low concentrations of oxy-chlorine anion. Thus, ASEPTROL materials provide a way to efficiently generate chlorine dioxide at substantially neutral pH, thus avoiding problems existing with earlier, acidic chlorine dioxide-based products.

In some embodiments, the composition further comprises a thickener component which renders the composition a thickened aqueous fluid. To prepare a thickened aqueous composition comprising chlorine dioxide that is substantially non-cytotoxic and, in some embodiments, non-irritating, the substantially pure chlorine dioxide solution can be combined with a thickener component and an aqueous medium.

The aqueous thickened fluid composition used in practicing the method may comprise any thickener component in an aqueous medium, wherein the thickened fluid composition is non-cytotoxic and/or non-irritating to soft tissues. In exemplary embodiments, the thickener is not adversely affected by the chlorine dioxide on the time scale of composition preparation and use in treatment. Many thickener agents are known in the art, including, but not limited to carbomers (e.g., CARBOPOL thickeners, Lubrizol Corp., Wickliffe, Ohio), sodium carboxymethylcellulose (NaCMC), ethylcellulose, hydroxyethylcellulose, hydroxypropyl methylcellulose (HPMC), natural smectite clays (e.g., VEEGEM, R.T. Vanderbilt Co., Norwalk, Conn.), synthetic clays (e.g., LAPONITE (Southern Clay Products, Gonzales, Tex.), methylcellulose, superabsorbent polymers such as polyacrylates (e.g., LUQUASORB 1010, BASF, Florham Park, N.J.), poloxamers (PLURONIC, BASF, Florham Park, N.J.), polyvinyl alcohol, sodium alginate, tragacanth, and xanthan gum. Such thickening agents may be categorized into four groups: natural hydrocolloids (also referred to as "gum"), semisynthetic hydrocolloids, synthetic hydrocolloids, and clay. Some examples of natural hydrocolloids include acacia, tragacanth, alginic acid, carrageenan, locust bean gum, guar gum, and gelatin. Non-limiting examples of semisynthetic hydrocolloids include methylcellulose and sodium carboxymethylcellulose. Some examples of synthetic hydrocolloids (also referred to as "polymers" including polymers, cross-linked polymers, and copolymers) include polyacrylates, superabsorbent polymers, high molecular weight polyethylene glycols and polypropylene glycols, polyethylene oxides and CARBOPOL. Non-limiting examples of clay (including swelling clay) include LAPONITE, attapulgite, bentonite, and VEEGUM. In some embodiments, the thickener component can be a semisynthetic hydrocolloid. An exemplary thickener component is hydroxypropyl methylcellulose or a carboxymethylcellulose (CMC).

In preparing a non-cytotoxic composition, one or more components of a composition may be combined prior to the time of preparation of a composition. Alternatively, all components of a composition may be prepared at the time of use. For either non-cytotoxic solutions or non-cytotoxic thickened compositions, optional other components suitable for the intended use of the non-cytotoxic chlorine dioxide solution, as described elsewhere herein, may be included. Chlorine dioxide in solution will decompose over time. To avoid problems arising from such decomposition, including loss of efficacy and generation of chlorite anions, the substantially pure chlorine dioxide solution is preferably prepared immediately before its dilution or its combination with a thickener component and an aqueous medium.

In addition, in some embodiments, a thickened composition comprising chlorine dioxide can be prepared immediately before its use. "Immediately before" as used herein, refers to a period no greater than that which would result in diminished efficacy or evidence of cytotoxicity. Generally, "immediately before" is less than about 14 days, and preferably no greater than about 24 hours and more preferably no greater than about 2 hours. In exemplary embodiments, the substantially pure chlorine dioxide solution is prepared within about 8 hours of the preparation of the composition. Precautions are also taken to avoid exposing the chlorine dioxide solution or the prepared composition to strong ultraviolet light or elevated temperature (e.g., temperature greater than ambient temperature, about 25° C.).

A substantially non-cytotoxic thickened composition comprising chlorine dioxide may also be prepared using a particulate precursor of $ClO_2$ and an aqueous thickened fluid composition. Chlorine dioxide-forming components include metal chlorites, metal chlorates, an acid source, and an optional halogen source. The particulate precursor may comprise one of these or any combination of these. An exemplary particulate precursor is an ASEPTROL product. An exemplary ASEPTROL product is ASEPTROL S-Tab2. ASEPTROL S-Tab2 has the following chemical composition by weight (%): $NaClO_2$ (7%); $NaHSO_4$ (12%); NaDCC (1%); NaCl (40%); $MgCl_2$ (40%). Example 4 of U.S. Pat. No. 6,432,322 describes an exemplary manufacture process of S-Tab2. Granules can be produced, either by comminuting pressed S-Tab2 tablets, or by dry roller compaction of the non-pressed powder of the S-Tab2 components, followed by breakup of the resultant compacted ribbon or briquettes, and then screening to obtain the desired size granule. Upon exposure to water or an aqueous thickened fluid, chlorine dioxide is generated from the ASEPTROL granules. In one embodiment, a substantially non-cytotoxic composition comprising chlorine dioxide is prepared by combining −40 mesh granules with an aqueous thickened fluid. In one embodiment, the thickener component of the thickened fluid is carboxymethylcellulose or HPMC. The skilled artisan will recognize that chlorine dioxide production in the thickened fluid composition prepared using a particulate precursor of $ClO_2$, while rapid, is not instantaneous. Thus, sufficient time for the generation of chlorine dioxide, and corresponding consumption of chlorite anion, is necessary to obtain a substantially non-cytotoxic thickened fluid composition. The skilled artisan can readily determine what length of time is sufficient, in view of the teachings in this disclosure and the knowledge of the art.

In some embodiments, the aqueous thickened fluid is prepared sufficiently in advance of combining with the ASEPTROL granules to enable the complete hydration of the thickener component. In one embodiment, the thickened fluid composition is formed by adding high viscosity NaCMC powder to distilled water. The NaCMC is allowed to hydrate for at least 8 hours, and then the mixture is stirred to homogenize it. A substantially non-cytotoxic composition is then prepared by mixing the sized ASEPTROL granules with the NaCMC thickened fluid. Contact with the aqueous medium in the hydrated NaCMC mixture activates the ASEPTROL granules and chlorine dioxide is generated.

In another embodiment, the substantially non-cytotoxic thickened fluid composition may also be formed at the site of intended use. For instance, a body fluid such as mucus of mucosal tissue, saliva, wound exudate or humid vapor such as exhaled air, may serve as the aqueous medium to activate particulate precursors of chlorine dioxide, such as ASEPTROL granules. In one embodiment, the mixture may be particulates in the form of a powder and mixed in a layer of thickener component thereby forming a thickened matrix. The matrix may be applied directly to a mucosal tissue or wound, wherein exposure to moisture present in the tissue activates production of chlorine dioxide to form a substantially non-cytotoxic composition. Alternatively, the matrix may be moistened immediately prior to use and then applied to any tissue.

In an embodiment, the substantially non-cytotoxic and/or non-irritating composition consists essentially of chlorine dioxide as the active pharmaceutical ingredient (API). In other embodiments, the composition comprises chlorine dioxide in combination with at least one other API, such as an antimicrobial, topical anesthetic, topical analgesic, steroid or combination thereof. The composition optionally comprises one or more other components. Such components include, but are not limited to, coloring agents and fragrances. Other optional components include: enzymes, malodor controlling agents, and the like. Exemplary antimicrobials include, but are not limited to, gatifloxacin, clindamycin, gentiamicin, ceftazidime, an aminoglycoside such as tobramyin and streptomycin, amphotericin B, itraconazole, ketoconazole, miconazole, nystatin, neomycin, ribaximin, clindamycin, metronidazole, polymixin B, proguanil, econazole, and fluconazole.

In some embodiments, all optional components are relatively resistant to oxidation by chlorine dioxide, since oxidation of composition components by chlorine dioxide will reduce the available chlorine dioxide for oxidation for its intended function. "Relatively resistant" means that in the time scale of preparing and using the chlorine dioxide-containing composition in an application, the function of the optional component is not unacceptably diminished, and the composition retains an acceptable level of efficacy/potency with respect to the chlorine dioxide and remains substantially non-cytotoxic. In some embodiments, the composition can remain substantially non-irritating. Guidance regarding identifying resistant components is provided in commonly-assigned U.S. patent application entitled "Additives for Chlorine Dioxide-Containing Compositions," serial number 61/299,999, filed Jan. 31, 2010.

The substantially non-cytotoxic and/or substantially non-irritating composition can be delivered to tissue using any method known in the art. Formulations can include ointment, gel, cream, lotion, plasters, transdermal patches, inserts, rinses, and the like. For oral applications, the composition can also be delivered to a tooth surface or oral tissue by dental tray, dental film, or dental strip. A dental strip refers to a substantially planar object made of a plastic backbone that is sufficiently flexible to affix to teeth. A dental film refers to a substantially planar object made of a pliable, conformable material that can be substantially fitted to the surface of teeth. Optionally, the dental strip is dissolvable in an aqueous medium, such as saliva.

2. Devices and Compositions for Non-Cytotoxic Administration

In home embodiments, the method can be practiced with a device or composition that delivers a substantially oxy-chlorine anion free chlorine dioxide composition to the wound, tooth surface, or to the infected oral cavity tissue. Such devices, compositions, systems and methods for administration of a composition comprising chlorine dioxide and oxy-chlorine anions in a way that the chlorine dioxide reaches the target tissue in an efficacious amount, but the oxy-chlorine anions are substantially inhibited from irritating target tissue or peripheral tissue not targeted for treatment, are described in commonly-assigned U.S. application Ser. Nos. 12/502,845, 12/502,858 and 12/502,877, filed Jul. 14, 2009, entitled "Methods, Systems and Devices for Administration of Chlorine Dioxide." Generally, the method comprises providing a chlorine dioxide source that includes either chlorine dioxide itself or chlorine dioxide-generating components, and further includes the oxy-chlorine anions that cause cytotoxicity to tissues; and further providing an oxy-chlorine anion barrier that substantially prohibits passage therethrough of the oxy-chlorine anions and permits passage therethrough of chlorine dioxide. In some embodiments, the oxy-chlorine anion barrier can also substantially inhibit the passage therethrough of protons. The chlorine dioxide source is applied to the tissue with the oxy-chlorine anion barrier interposed between the chlorine dioxide source and the tissue, thus preventing or substantially minimizing the oxy-chlorine anion from reaching the tissue, thereby enabling delivery of a substantially oxy-chlorine anion free chlorine dioxide composition to the tissue.

The chlorine dioxide that comes into contact with the tissue is substantially oxy-chlorine anion free. In one embodiment, the substantially oxy-chlorine anion free chlorine dioxide that contacts the tissue comprises zero milligram (mg) oxy-chlorine anion per gram to no more than about 0.25 mg oxy-chlorine anion per gram, or from zero to 0.24, 0.23, 0.22, 0.21, or 0.20 mg oxy-chlorine anion per gram composition, or from zero to 0.19, 0.18, 0.17, 0.16, 0.15, 0.14, 0.13, 0.12, 0.11, or 0.10 mg oxy-chlorine anion per gram composition, or from zero to 0.09, 0.08, 0.07, 0.06, 0.05 or 0.04 mg oxy-chlorine anion per gram composition, absent other constituents that contribute to cytotoxicity, and is therefore substantially non-cytotoxic. In some embodiments, the substantially oxy-chlorine anion free chlorine dioxide comprises less than about 400 milligrams per square meter of contact area, less than about 375 mg/m$^2$, less than about 350 mg/m$^2$, than about 325 mg/m$^2$, or than about 300 mg/m$^2$ oxy-chlorine anions. In some embodiments, the substantially oxy-chlorine anion free chlorine dioxide comprises from zero to less than about 200 mg/m$^2$ oxy-chlorine anions. In other embodiments, the substantially oxy-chlorine anion free chlorine dioxide comprises from zero to less than about 100 mg/m$^2$ oxy-chlorine anions.

The chlorine dioxide source can comprise any chlorine dioxide-containing composition or ingredients capable of forming chlorine dioxide in situ. In exemplary embodiments, the ingredients present in the chlorine dioxide source are compatible with the oxy-chlorine anion barrier during the practice of the method, as well as any pre-use period during which the ingredients are in contact with the barrier. By "compatible" is meant the ingredients do not adversely affect to an unacceptable degree the concentration of chlorine dioxide in the chlorine dioxide source, the inhibition of passage of oxy-chlorine anions, or the permitted passage of chlorine dioxide by the barrier.

The barrier may be in the form of a layer between the chlorine dioxide source and the target tissue. In one aspect, the oxy-chlorine barrier, without the chlorine dioxide source, is applied to the tissue first. The chlorine dioxide source is then applied to the barrier layer. In other embodiments, the chlorine dioxide source can be applied to the barrier first, and the combination can be then applied to the tissue, wherein the barrier layer contacts the tissue. In embodiments where the chlorine dioxide source comprises chlorine dioxide-generating components, the generation of chlorine dioxide may be activated before, during, and/or after application of the barrier (with or without the chlorine dioxide source) to the target tissue.

In another embodiment, the target tissue may be contacted with a chlorine dioxide source containing a substantially non-cytotoxic and substantially non-irritating amount of oxy-chlorine anions while a second chlorine dioxide source may be located on the side of a barrier opposite the target tissue such that additional chlorine dioxide from the second source may pass through the barrier to contact the target tissue but passage through the barrier of oxy-chlorine anions in the second source is inhibited.

In another embodiment, the chlorine dioxide source may be dispersed in a matrix comprising one or more barrier substances, such that the oxy-chlorine anions are sequestered away from the tissue, while the chlorine dioxide passes through the barrier substance, if necessary, and the matrix to contact the target tissue. In this embodiment, the matrix is applied to the tissue directly or to an optional intervening tissue-contacting layer. In one aspect, the matrix itself is the barrier substance. Exemplary matrix materials that may also function as the barrier include waxes such as paraffin wax, polyethylene, petrolatum, polysiloxanes, polyvinyl alcohol, ethylene-vinyl acetate (EVA), polyurethanes, mixtures thereof, and the like. In another aspect, the chlorine dioxide source can be coated or encapsulated by the barrier substance. Exemplary barrier substances include polyurethane, polypropylene, polytetrafluoroethylene, polyvinylidene difluoride, polyvinylidene dichloride, combination of polydimethylsiloxane and polytetrafluoroethylene, polystyrene, cellulose acetate, polysiloxane, polyethylene oxide, polyacrylates, mineral oil, paraffin wax, polyisobutylene, polybutene and combinations thereof. Exemplary barrier substances also comprise compounds that bind to oxy-chlorine anions with high affinity and that impede or stop anion migration or diffusion such that a substantially oxy-chlorine anion free chlorine dioxide composition can be delivered to a tissue. The compound may form an insoluble precipitate with the oxy-chlorine anion, thereby impeding or stopping diffusion. Alternatively, the compound is immobilized on a substance or material, thereby impeding diffusion or migration. The compound may be cationic, such as ammonium, pyridinium, imidazolium, phosphonium, and sulfonium, and other positively charged compounds that may be part of the matrix. Optionally, the compound can be immobilized on an oxy-chlorine anion barrier material, to the matrix or on the optional backing layer.

Various materials and membranes can be used as an oxy-chlorine anion barrier. The barrier can be in any form, and is typically either a fluid or a solid.

In some embodiments, the oxy-chlorine anion barrier is a fluid, such a petrolatum. In this embodiment, the fluid can be applied to the tissue first, or to an intervening tissue-contacting layer, to form the barrier as a layer and then chlorine dioxide source subsequently applied to the fluid barrier layer. The chlorine dioxide source can be applied as a particulate or can be encompassed in a material to form a film.

In some embodiments, the oxy-chlorine anion barrier is a nonporous membrane. The membrane can be any thickness and can be a single layer or plural layers, provided the membrane remains permeable to chlorine dioxide and substantially non-permeable to oxy-chlorine anions. An exemplary nonporous material is a polyurethane membrane. In some embodiments, the polyurethane membrane is from about 30 to about 100 microns, such as from about 38 to about 76 microns thick. Exemplary polyurethane membranes commercially available include CoTran™ 9701 (3M™ Drug Delivery Systems, St. Paul, Minn.) and ELASTOLLAN (BASF Corp., Wyandotte, Mich.). ELASTOLLAN products are polyether-based thermoplastic polyurethane. A specific example of ELASTOLLAN is ELASTOLLAN 1185A10.

In some embodiments, the oxy-chlorine anion barrier is a microporous membrane permeable to chlorine dioxide and substantially non-permeable to oxy-chlorine anions. The microporous membrane can be any thickness and can be a single layer or plural layers, provided the membrane remains permeable to chlorine dioxide and substantially non-permeable to oxy-chlorine anions. In one example, the microporous membrane can comprise thermo-mechanically expanded polytetrafluoroethylene (e.g., Goretex®) or polyvinylidenedifluoride (PVDF). See, for instance, U.S. Pat. No. 4,683,039. The procedure for formation of an expanded polytetrafluoroethylene is described in U.S. Pat. No. 3,953,566. An exemplary polytetrafluoroethylene (PTFE) membrane, interpenetrating polymer network (IPN) of polydimethylsiloxane and PTFE, is described in U.S. Pat. Nos. 4,832,009, 4,945,125, and 5,980,923. A commercially-available product of this type, Silon-IPN (Bio Med Sciences Inc., Allentown, Pa.), is a single layer and is available in thicknesses between 10 to 750 microns. In one embodiment, the microporous membrane is an IPN of silicone and PTFE having a thickness of about 16 microns. In another example, the membrane is microporous polypropylene film. An exemplary microporous polypropylene film is the material commercially-available from CHEMPLEX Industries (Palm City, Fla.), which is a single layer membrane about 25 microns thick, having a porosity of 55% and a pore size of about 0.21 microns×0.05 microns. The microporous membrane material can be provided as a composite with supporting materials to provide the structural strength required for use. In some embodiments, the membrane is hydrophobic, wherein the hydrophobic nature of the membrane prevents both an aqueous reaction medium and an aqueous recipient medium from passing through the membrane, while allowing molecular diffusion of chlorine dioxide. Features to consider for the materials used for such a barrier include: hydrophobicity of the microporous material, pore size, thickness, and chemical stability towards the attack of chlorine dioxide, chlorine, chlorite, chlorate, chloride, acid, and base.

Various other materials and membranes can be used to form the barrier. For example, the barrier can comprise a microperforated polyolefin membrane; a polystyrene film that is substantially permeable to chlorine dioxide and substantially impermeable to ionic components of the composition; a pervaporation membrane formed from a polymeric material having a relatively open polymeric structure; a cellulose acetate film composite; a polysiloxane or polyurethane material; or a wax. Of course, for contact with mucosal or dermal tissues, the microporous barrier should be substantially non-irritating and substantially non-cytotoxic, particularly in the time scale of typical use of the device and composition.

The pore sizes in the barrier may vary widely, depending on the desired flow rate of the chlorine dioxide through the barrier. The pores should not be so small as to prevent chlorine dioxide gas flow therethrough but also should not be so large that liquid flow is permitted. In one embodiment, the pore size is about 0.21 microns×0.05 microns. The quantity and size of the pores of the barrier can vary widely, depending upon the temperature of the application, the hydrophobicity of the barrier material, the thickness of the barrier material, and also depending upon the desired flow rate of chlorine dioxide through the barrier. Fewer and smaller pores are needed for a given chlorine dioxide flow rate at higher temperature relative to lower temperature, as the vapor pressure of chlorine dioxide from the chlorine dioxide source is higher at the higher temperature. More and larger pores can be used with a highly hydrophobic barrier material, such as PTFE, compared to a less hydrophobic material, such as polyurethane, since the tendency for an aqueous chlorine dioxide source to flow through pores of a highly hydrophobic barrier is lower than it is through the pores of a less hydrophobic barrier. Considerations of barrier strength also dictate the porosity chosen.

Generally, the barrier porosity varies from about 1 to about 98%, from about 25 to about 98%, or from about 50% to about 98%.

Also provided are systems, compositions, and devices useful for practicing the method. In one aspect, a system is provided for delivering a substantially oxy-chlorine anion free chlorine dioxide to a tissue. A typical system comprises a chlorine dioxide source that includes chlorine dioxide or chlorine dioxide-generating components, and oxy-chlorine anions as a first system component; and an oxy-chlorine anion barrier as a second system component, the barrier to be interposed between the chlorine dioxide source and the tissue, wherein the barrier substantially prohibits passage of the oxy-chlorine anions and permits passage of the substantially oxy-chlorine anion free chlorine dioxide composition, thereby enabling delivery of the substantially oxy-chlorine anion free chlorine dioxide to the tissue.

Compositions and devices are also provided to implement the methods and systems described above. Thus, one aspect features a composition for delivering a substantially oxy-chlorine anion free chlorine dioxide composition to a tissue. The composition comprises a matrix that includes a chlorine dioxide source comprising chlorine dioxide or chlorine dioxide-generating components, as well as oxy-chlorine anions, and at least one barrier substance that substantially prohibits passage of the oxy-chlorine anions but permits passage of the chlorine dioxide, thereby enabling delivery of the substantially oxy-chlorine anion free chlorine dioxide to the tissue. In one embodiment, the matrix can be a aqueous matrix, or a hydrophobic or anhydrous matrix such as petrolatum. In some embodiments, the matrix itself is the barrier substance. For instance, the matrix can be nonpolar or weakly polar for inhibiting diffusion of oxy-chlorine anions while permitting diffusion of chlorine dioxide.

The bulk of the matrix can be the barrier substance, or the matrix can comprise a sufficient amount of the barrier substance to carry out the selective delivery of the chlorine dioxide to the tissue. For instance, the matrix can comprise a polymeric material in which reactants or precursors for the formation of chlorine dioxide are embedded or dispersed, wherein the polymeric material is permeable to chlorine dioxide but substantially impermeable to oxy-chlorine anions. See, e.g., U.S. Pat. No. 7,273,567, which describes a composition comprising reactants or precursors and an energy-activatable catalyst embedded in polyethylene, which are activated to produce chlorine dioxide by exposure to light waves, and more particularly, by exposure to ultraviolet radiation.

In some embodiments, the matrix can be an adhesive matrix, such as an adhesive polymer matrix. Polymers useful in such adhesive matrices are substantially permeable to chlorine dioxide and are preferably relatively resistant to oxidation by chlorine dioxide so as to limit possible degradation of the polymer and possible consequential change in adhesion. Adhesive polymers are known in the art. See, e.g., U.S. Pat. No. 7,384,650.

The composition can be applied to the tissue, e.g., by spreading it on or otherwise applying it to the tissue, or by incorporating it into a delivery device, such as described below.

Various delivery devices are envisioned for delivering a composition comprising chlorine dioxide and oxy-chlorine anions to target tissue such that an efficacious amount of chlorine dioxide contacts the target tissue, while the oxy-chlorine anions are substantially inhibited or prevented from contacting the tissue. The substantial inhibition reduces, minimizes, or precludes damage or irritation to, the target tissue and any surrounding or peripheral tissues.

The devices are typically directionally oriented to comprise a layer distal to the tissue to be contacted and a layer proximal to the tissue to be contacted. The distal layer is also referred to herein as a backing layer. The devices may further comprise a release liner affixed to the tissue-contacting layer, to be removed prior to applying the device to the tissue. In one embodiment, the device comprises a layer comprising the chlorine dioxide source and a barrier layer. In another embodiment, the device comprises (1) a backing layer, (2) a layer comprising the chlorine dioxide source, and (3) a barrier layer. The barrier layer can be adapted to contact the non-oral tissue, or another tissue-contacting layer may be present between the barrier layer and the tissue. The barrier layer or the additional tissue-contacting layer can be adhesive. The optional additional tissue-contacting layer is also substantially permeable to chlorine dioxide. In some embodiments, the barrier layer can be made from a thermo-mechanically expanded polytetrafluoroethylene film. In some embodiments, the chlorine dioxide source is a particulate precursor of chlorine dioxide, such as granules of ASEPTROL.

Generally, the backing layer can be made of any suitable material that is substantially impermeable to chlorine dioxide and other components of the chlorine dioxide source. The backing layer can serve as a protective cover for the matrix layer and can also provide a support function. Exemplary materials for the backing layer include films of high and low-density polyethylene, polyvinylidene dichloride (PVDC), polyvinylidene difluoride (PVDF), polypropylene, polyurethane, metal foils, and the like.

The optional tissue-contacting layer can be any material that is substantially permeable to chlorine dioxide. The optional tissue-contacting layer can be an absorbent material. Non-limiting examples for this layer include cotton or other natural fiber or synthetic fiber fabrics or meshes, foams and mats.

In another embodiment, the device comprises a backing layer and a matrix as described above, in which is dispersed the chlorine dioxide source and which comprises at least one barrier substance. The matrix can be adapted for contacting the tissue, or an additional tissue-contacting layer may be present. Either the matrix or the additional tissue-contacting layer can be adhesive. Typically, the matrix is prepared and then coated onto the backing layer.

Any method in the art for preparing chlorine dioxide may be used as the chlorine dioxide source to make chlorine dioxide in the devices and compositions that deliver a substantially oxy-chlorine anion free chlorine dioxide composition. For instance, there are a number of methods of preparing chlorine dioxide by reacting chlorite ions in water to produce chlorine dioxide gas dissolved in water. The traditional method for preparing chlorine dioxide involves reacting sodium chlorite with gaseous chlorine ($Cl_2(g)$), hypochlorous acid (HOCl), or hydrochloric acid (HCl). However, because the kinetics of chlorine dioxide formation are high order in chlorite anion concentration, chlorine dioxide generation is generally done at high concentration (>1000 ppm), the resulting chlorine dioxide containing solution typically must be diluted for the use concentration of a given application. Chlorine dioxide may also be prepared from chlorate anion by either acidification or a combination of acidification and reduction. Chlorine dioxide can also be produced by reacting chlorite ions with organic acid anhydrides.

Chlorine dioxide-generating compositions, which are comprised of materials that will generate chlorine dioxide gas upon contact with water vapor, are known in the art. See, e.g., commonly-assigned U.S. Pat. Nos. 6,077,495; 6,294,108; and 7,220,367. U.S. Pat. No. 6,046,243 discloses composites of chlorite salt dissolved in a hydrophilic material and an acid releasing agent in a hydrophobic material. The composite generates chlorine dioxide upon exposure to moisture. Commonly-assigned U.S. Pat. Publication No. 2006/0024369 discloses a chlorine dioxide-generating composite comprising a chlorine dioxide-generating material integrated into an organic matrix. Chlorine dioxide is generated when the composite is exposed to water vapor or electromagnetic energy. Chlorine dioxide generation from a dry or anhydrous chlorine dioxide-generating composition by activation with a dry polar material is disclosed in commonly-assigned co-pending U.S. Provisional Application No. 61/153,847. U.S. Pat. No. 7,273,567 describes a method of preparing chlorine dioxide from a composition comprising a source of chlorite anions and an energy-activatable catalyst. Exposure of the composition to the appropriate electromagnetic energy activates the catalyst which in turn catalyzes production of chlorine dioxide gas.

Chlorine dioxide solutions can also be produced from solid mixtures, including powders, granules, and solid compacts such as tablets and briquettes, which are comprised of components that will generate chlorine dioxide gas when contacted with liquid water. See, for instance, commonly-assigned U.S. Pat. Nos. 6,432,322; 6,699,404; and 7,182,883; and U.S. Pat. Publication Nos. 2006/0169949 and 2007/0172412. In some embodiments, chlorine dioxide is generated from a composition comprising a particulate precursor of chlorine dioxide. Thus, the chlorine dioxide source comprises or consists essentially of a particulate precursor of chlorine dioxide. The particulate precursor employed can be an ASEPTROL product, such as ASEPTROL S-Tab2 and ASEPTROL S-Tab10. ASEPTROL S-Tab2 has the following chemical composition by weight (%): $NaClO_2$ (7%); $NaHSO_4$ (12%); sodium dichloroisocyanurate dihydrate (NaDCC) (1%); NaCl (40%); $MgCl_2$ (40%). Example 4 of U.S. Pat. No. 6,432,322 describes an exemplary manufacture process of S-Tab2 tablets. ASEPTROL S-Tab10 has the following chemical composition by weight (%): $NaClO_2$ (26%); $NaHSO_4$ (26%); NaDCC (7%); NaCl (20%); $MgCl_2$ (21%). Example 5 of U.S. Pat. No. 6,432,322 describes an exemplary manufacture process of S-Tab10 tablets.

As described elsewhere herein, activation of chlorine dioxide generation can be prior to administration by contact of the chlorine dioxide-generating components with the appropriate agent (e.g., aqueous medium, electromagnetic energy, etc). Alternatively, chlorine dioxide generation initiated in situ, by contact with an aqueous medium, such as mucus, saliva, water, wound exudate or the like.

Armed with this disclosure and the knowledge in the art, it is within the skill of the skilled artisan to physically adapt the devices and compositions that deliver a substantially oxy-chlorine anion free chlorine dioxide composition for contact with a wound to treat the wound, contact with a tooth surface for tooth whitening or contact with oral mucosal tissue such as gingival mucosal tissue to treat an oral cavity infection. For instance, the devices and compositions for use in oral applications can themselves be in the form of a dental tray or can be adapted to be delivered by means of a dental tray.

3. Treatment Regimens

In an embodiment, the method can comprise a single administration of the composition comprising a chlorine dioxide source. In another embodiment, the method comprises one or more iterations of the contacting step, wherein each subsequent administration step is substantially contiguous to the previous iteration. In some embodiments, the method comprises three, four, five, or more substantially contiguous iterations of an administration step. Each iteration can be identical in terms of dose and contact duration, each iteration can be different, or a combination of both. As shown herein, multiple substantially contiguous applications to a tissue of a composition comprising a chlorine dioxide source can be efficacious in reducing bacterial count in a wound. As further shown herein, multiple substantially contiguous applications of composition comprising a chlorine dioxide source is efficacious in tooth whitening. Specifically, it was found that for a given total dosage (Concentration of chlorine dioxide in parts-per-million×total time of exposure in min; ppm-min), statistically significantly improved tooth whitening can be achieved by using more frequent, shorter duration applications in a substantially contiguous manner. Each application uses a fresh specimen of the composition comprising a chlorine dioxide source. By "fresh specimen" is meant a specimen of composition that has not been previously exposed to a biological tissue. Accordingly, a fresh specimen has undergone minimal-to-no chlorine dioxide decay. In exemplary embodiments, the composition for a treatment is freshly made. As used herein, "freshly made" means that the addition of chlorine dioxide to the other components of the final composition occurs within about one hour, within about 30 minutes, or within about 15 minutes before contacting a tissue with the composition. A freshly made composition has therefore undergone minimal-to-no chlorine dioxide decay.

In the iterative embodiments, while the composition comprising a chlorine dioxide source can be the same in the iterations, it is more common that the composition in each iteration is fresh. In other words, the composition in one iteration is replaced with a fresh specimen of the composition. In embodiments using devices or compositions to deliver a substantially oxy-chlorine anion free chlorine dioxide composition to a tissue, the device or composition in one iteration is replaced with a fresh device or specimen of composition. By "fresh device" is meant a delivery device whose tissue interface for delivering $ClO_2$ has not been previously exposed to a biological tissue. Accordingly, a fresh device has undergone minimal-to-no chlorine dioxide decay. In some embodiments, a single batch of the composition comprising a chlorine dioxide source is prepared at the start of treatment in a volume sufficient to cover the entire series of contiguous iterations, and fresh specimens are taken from the single batch for each iteration. In other embodiments, the composition comprising a chlorine dioxide is prepared fresh before each iteration.

In other embodiments, the method can further comprise alternating treatment steps wherein one step comprises administration of a composition comprising a chlorine dioxide source and a second step comprises administration of a composition comprising a second, non-chlorine-dioxide therapeutic agent. These steps may take place in any order and in multiple iterations. Consecutive steps may comprise the same composition or different compositions. Examples of other non-chlorine dioxide therapeutic agents are listed elsewhere herein.

The method can comprise two or more sequential steps of administration of the composition comprising a chlorine dioxide source, followed by at least one step of administration of the other therapeutic agent. The number and/and duration of administration steps with the composition comprising a chlorine dioxide source can be the same or different as the number and/or duration of administrations with the second therapeutic composition. The composition comprising a chlorine dioxide source can be identical in the plural steps or can be different, such as a different concentration of chlorine dioxide. Similarly, the second therapeutic agent composition can be identical in the plural steps or may be different. Likewise, the duration of treatment steps can be the same or different for the composition comprising a chlorine dioxide source and for the second therapeutic agent composition.

Treatment can occur as frequently as several times daily, or can occur less frequently, such as once, once a day, once a week, once every two weeks, once a month, or even less frequently, such as once every several months or even once a year or less. The frequency of treatment suitable for achieving the desired efficacy will be readily apparent to the skilled artisan and will depend upon any number of factors, such as, but not limited to, the type and severity of the disease/disorder being treated and the method of contacting the tissue, etc. As discussed elsewhere herein, a treatment can comprise one episode of tissue contact or more than one episode. Treatment episodes can be: substantially contiguous, separated in time (e.g., a few hours to a few days, a few days to a few weeks, and also longer intervals including several months to a year or more) or both. In some embodiments, treatment comprises at least two substantially contiguous episodes of tissue contact. The contiguous episodes can be the same duration in time such as about 7.5 minutes or different durations of time such as 5 minutes and 10 minutes. In some embodiments for whitening a tooth surface, treatment is at least four substantially contiguous episodes of 7.5 minutes each. In one aspect of this embodiment, the composition comprises between about 100 to 400 ppm $ClO_2$, or about 150 to about 200 ppm $ClO_2$. The pH of the composition in these embodiments can be about 4 to 7, or about 5 to 6.

In an embodiment for treating wounds, a combination therapy including debridement is envisioned. Debridement is the process of removing damaged tissue, necrotic tissue and/or infected tissue in a wound. Debridement is believed to be benefit wound healing by improving the healing potential of the remaining healthy tissue. In general, debridement can either be done surgically, mechanically, chemically, and/or with maggot therapy, and these procedures are well-known in the art. Debridement can also be achieved by use of ultrasonic energy. In this case, the ultrasound treatment would precede the step of contacting the wound with a chlorine dioxide composition.

In an embodiment, a combination therapy including high frequency mechanical energy to improve contact of the chlorine dioxide with the target tissue is envisioned. An exemplary frequency range is about 5 Hz to about 5 MHz.

In one embodiment, the high frequency mechanical energy is ultrasound. Ultrasound is sound energy of frequency >20 kHz to about 10 MHz, which is above the normal range of human perception, and with power from greater than 0 to about 5 $W/cm^2$. It may produce a number of biophysical effects that are relevant to wound healing. These include alterations in cellular protein synthesis and release, blood flow and vascular permeability, angiogenesis, and collagen content and alignment. Wound and tissue care methods using ultrasonic energy in wound care requires ultrasonic energy to be emitted from a radiation surface to the wound or tissue surface. In one embodiment, a tissue to which a composition comprising a chlorine dioxide source has been applied is then exposed to ultrasonic energy to increase penetration of the chlorine dioxide into the tissue. Increasing tissue penetration is envisioned to improve wound healing by increasing contact of chlorine dioxide with pathogens located below the surface of the wound. In certain embodiments, reduction in bacterial count in a combination therapy including ultrasonication (in comparison to the same therapy in the absence of the ultrasonication) can be from at least about 1 log, 2, logs, 3 logs, 4 logs, up to a substantially complete log kill (e.g., substantially no bacteria detectable). For instance, for a wound having an initial total bacterial count of 8 log prior to treatment, a substantially complete log kill is 8 logs. Bacterial count can be assessed by any method known in the art. An exemplary method for assessing bacterial count is by obtaining a tissue sample of the infected tissue, preparing serial dilutions from the tissue sample, and plating the dilutions to culture and assess bacterial count. Assessment before and after treatment is performed to assess the reduction in bacterial log.

In some embodiments, the ultrasound frequency can be from about 1 kHz to about 100 kHz, about 10 kHz to about 50 kHz, or about 20 kHz to about 40 kHz and all integer values therebetween. For instance, in certain embodiments using ultrasonic energy, the frequency ranges from 20 kHz, 21, 22, 23, 24, 25 to 40 kHz, from 26 kHz, 27, 28, 29, 30, to 40 kHz, from 31, 32, 33, 34, 35, to 40 kHz, or from 36 kHz, 37, 38, 39 to 40 kHz. In some embodiments, at least two different ultrasonic wave frequencies administered intermittently can be used. In some embodiments, power intensities can range from about 0.1 to about 5 $W/cm^2$, including all one-tenth values therebetween. Therefore, power intensities can be from about 0.1, 0.2, 0.3, 0.4, 0.5 to about 5 $W/cm^2$ from 0.6, 0.7, 0.8, 0.9, 1.0 to about 4.5 $W/cm^2$, from 1.1, 1.2, 1.3, 1.4, 1.5, 1.6, 1.7. 1.8, 1.9 to 4.5 $W/cm^2$, from 2.0, 2.1, 2.2, 2.3, 2.4, 2.5, 2.6, 2.7. 2.8, 2.9 to 4.5 $W/cm^2$, from 3.0, 3.1, 3.2, 3.3, 3.4, 3.5, 3.6, 3.7. 3.8, 3.9 to 4.4 $W/cm^2$, or from 3.0, 3.1, 3.2, 3.3, 3.4, 3.5, 3.6, 3.7. 3.8, 3.9 to 4.0 $W/cm^2$. Duty cycle can range from about 20% to about 100%.

In some embodiments, at least two different power intensities administered intermittently can be used. Duty cycles can be the same or different. The duration of exposure to ultrasonic energy can be the same or different as the duration of exposure to the composition comprising a chlorine dioxide source, In some embodiments, the duration of ultrasonic energy for a single episode ranges from about 10 seconds to about 10 minutes, from about 10 seconds to about 5 minutes and from about 30 seconds to about 5 minutes, and all ranges inbetween. During a given treatment, multiple episodes of ultrasonic energy administration can be administered. The multiple episodes can be substantially contiguous or spaced out, for instance to permit cooling of tissue temperature between administrations of ultrasonic energy. In one embodiment, a tissue contacted with a composition comprising chlorine dioxide comprising about 100 to about 400 ppm chlorine dioxide is exposed to ultrasonic energy for between about 2-4 minutes using a frequency of about 20 to 40 kHz, with a power intensity from about 2 to about 4 $W/cm^2$ or from about 2.5 to about 3.5 $W/cm^2$, and a 40% duty cycle. Optionally, a tissue is contacted with at least two, three, four or more iterations of this ultrasound treatment.

Ultrasonication is also envisioned to improve alleviation of an oral tissue infection by improving penetration of chlorine dioxide into supra- and sub-gingival pockets. Ultrasound devices for oral application are known in the art. See, for instance, U.S. patent publication no. 20080209650 and U.S. Pat. Nos. 6,881,061 and 7,044,737.

In another embodiment, the method can comprise a combination therapy such as the addition of a second therapeutic agent. Combination therapy refers to the addition of another step intended to improve wound treatment or alleviation of oral tissue infection. In one embodiment, a combination therapy of contacting tissue with a chlorine dioxide composition and another API is envisioned. In one embodiment, the API is an antimicrobial, another therapeutic agent, or a combination thereof. Exemplary antimicrobials are disclosed elsewhere herein. Other therapeutic agents include topical anesthetics, steroids, analgesics and the like. Optionally, the method can further comprise the step of applying ultrasonic energy to the chlorine dioxide composition that has been contacted to the wound.

In another embodiment, a combination therapy including a pre-treatment is envisioned. The step of pre-treatment of the tissue is intended to increase penetration of the chlorine dioxide into the tissue. An exemplary pre-treatment includes, but is not limited to, contacting the tissue targeted for treatment with dimethylsulfoxide (DMSO) following by administering a composition comprising a chlorine dioxide source. Other exemplary pre-treatments include treating tissue with electromagnetic source following by administering a composition comprising a chlorine dioxide source, treating tissue with fatty acids following by administering a composition comprising a chlorine dioxide source, or treatment with sucrose esters, following by administering a composition comprising a chlorine dioxide source. See, e.g., U.S. Publication No. 20080208179 and U.S. Pat. No. 4,865,848.

4. Tissue Irrigation

In another embodiment, the methods of administering or contacting a tissue with a composition comprising a chlorine dioxide source can be practiced using irrigation. Irrigation of a tissue, such as a wound or an oral cavity infection, refers to the process of rinsing the tissue with a fluid composition. Irrigation can be either continuous or intermittent. Intermittent irrigation can be practiced using an automated irrigation device modified to deliver periodic applications of the composition to a tissue or can be practiced by manual irrigation, such as rinsing the wound or oral cavity with a volume of a composition comprising a chlorine dioxide source, and repeating this step iteratively using a fresh volume of the composition in each iteration. Continuous irrigation has the advantage that the effective concentration of chlorine dioxide per square inch of compromised skin is maintained at a substantially constant level over time and can be kept at an excess such that an efficacious amount is delivered, even though some chlorine dioxide may be consumed initially by reacting with organic matter, such as protein in wound exudate. As such, irrigation of a wound is expected to be equally effective or more effective than existing state-of-the-art products for wound treatment, e.g., silver-containing plaster or gels. Irrigation of infected oral tissue is expected to improve contact with supra- and sub-gingival pockets, which can improve reduction in bacterial count.

An irrigation system for use in the methods described herein is generally comprised of two components: a) an irrigation device comprising a chamber with inlet and outlet ports which covers the wound or other tissue to be irrigated; and a means of supplying solution into and draining solution out from the chamber; and b) a fluid composition comprising a chlorine dioxide source, which is supplied to the chamber so as to treat the wound or topical lesion. More specifically, the irrigation device can have five components: 1) a flexible, semi-rigid or rigid pouch or other containment chamber with inlet and outlet ports and with an opening that contacts at least a portion of tissue targeted to be irrigated; 2) a fluid supply and egress system which can be connected to the chamber ports so as to provide fluid to or drain fluid from the chamber; 3) a means of maintaining contact of the chamber to the tissue which surrounds the target tissue so as to form a tight substantially leak-proof seal; 4) an optional open cell foam or other porous material that can be placed inside the pouch to ensure a uniform distribution of flow; and 5) a fluid handling unit which supplies fluid to and/or allows fluid to exit the containment chamber.

The first component of the proposed system is the pouch or containment chamber. In exemplary embodiments, the outer surface of the pouch is made from one or more semi-rigid or rigid materials when suction is to be applied or from one or more soft flexible materials when the containment vessel is always under positive pressure. The three-dimensional shape of the chamber can assume multiple configurations. In one embodiment, the open portion of the chamber conforms to or is slightly larger than the boundary of the tissue that is being treated, and that the volume of the pouch is sufficient to provide an appropriate turnover of irrigation fluid. Another optional feature of the pouch is that it can be constructed of materials that are either antimicrobial or actively prevent biofilm formation.

The second component of this system is the system which allows fluid to flow into and out of the containment chamber. The system can be as simple as a single lumen device which only supports irrigation. However, in an embodiment, the tubing contains two or more lumens, one of which can be used to supply other agents such as a non-chlorine dioxide antimicrobial agent or an anesthetic agent to the pouch for use in tissue therapy, and one of which can be used to apply vacuum to the tissue area and/or can be used for suction.

The tubing system in an embodiment is a single or dual line flexible tube which is fabricated from flexible PVC or from a silicone based material. However, those skilled in the art will recognize that any suitable material can be used to fabricate the tubing, and will also recognize that the number of tubes chosen can vary, so long as they achieve the goals of the methods, devices and compositions disclosed. For example, one lumen can be used to apply a vacuum, and another lumen may be used to supply antibiotics, to irrigate a wound, or even to provide gases (e.g., oxygen) which may assist, for instance, in healing the wound. In addition, a third lumen can be used to conduct an electrical line which provides electrical stimulation. The lumens can be separated from one another, adjacent to one another, concentric to one another, or any combination thereof.

The third system component is a means of maintaining the chamber in contact with the skin so as to provide a tight, substantially leak-proof seal. The system can be relatively simple, such as a strap wrapped around the body in the location of the target tissue such that the strap holds a rigid chamber in place over the target tissue. In an embodiment, the attachment system is comprised of two components: 1) an adhesive wafer formed from a polyurethane film to which is laminated a suitable, skin-friendly adhesive, for example an acrylic adhesive; and 2) an annular wafer of similar construction wherein the urethane film is welded to the pouch material. The chamber is attached to the skin by first cutting a hole in the adhesive wafer which conforms to the outline of the wound or other topical lesion, and then attaching that wafer to the skin; the annular wafer attached to the pouch is then attached to the urethane film on the "skin side" adhesive wafer.

The fourth component is the flow distribution component which, optionally, is placed inside the irrigation chamber to ensure an even distribution of flow. This component can be a perforated membrane, an array of perforated tubes, or any other device known in the art for improving the uniformity of fluid flow. In an embodiment, the preferred flow distribution component is a porous open cell foam located in the opening of the chamber and in contact with the target tissue.

The fifth component is the fluid handling unit which supplies fluid to enter and/or allows fluid to exit the containment chamber. The fluid handling unit can be of any design which allows for the flow of fluid into or out of the chamber. For example, a fluid supply vessel can be located in a position of higher elevation relative to the chamber and be connected to the chamber by tubing such that fluid can flow into the chamber from the vessel by gravity. Similarly, a used-fluid receiving vessel can be located at an elevation lower than the chamber and be connected to the chamber by tubing such that used-fluid may flow out of the chamber into the fluid receiving vessel by gravity. In an embodiment, this component is a portable, lightweight, battery operated pump which attaches to the proximal end of at least one lumen of the tubing. Of course, other lumens can be attached to other items, such as antibiotic drip devices, electrical devices, etc.

In an embodiment, the fluid handling unit is designed such that it can be easily carried by a shoulder attachment or by attachment to the belt of the patient. In addition to the vacuum pump, in exemplary embodiments, the drain/suction unit also includes a reservoir, a battery power supply, and control switches for turning the drain/suction unit on or off.

Since chlorine dioxide can be lost to consumption by contaminants or diffusion through a material of some part of the irrigation device, the chlorine dioxide concentration within the containment chamber can be lower than that which exists in the fluid supply vessel containing the fresh composition comprising chlorine dioxide. It is important, then, to provide a sufficient flow and concentration of fresh chlorine dioxide mixture to the chamber to maintain the chlorine dioxide concentration within the chamber at a desired efficacious level. The chlorine dioxide concentration of the incoming fluid mixture should be at least as high as the desired concentration within the chamber. In certain embodiments, the incoming fluid mixture should be at a higher concentration than the target concentration. If the concentration of chlorine dioxide in the chamber is higher than the desired concentration, then the rate of flow into the enclosure may be reduced or the concentration of the incoming solution can be decreased, or both changes can be made until the chlorine dioxide concentration in the chamber falls to the desired level. If the concentration of chlorine dioxide in the chamber is lower than the desired concentration, then the rate of flow into the enclosure can be increased or the concentration of the incoming solution may be increased, or both changes can be made until the chlorine dioxide concentration in the chamber rises to the desired level.

The irrigation device described can be used with a substantially non-cytotoxic and/or substantially non-irritating composition comprising a chlorine dioxide source to contact the tissue with a continuous stream of the composition. In another embodiment, the irrigation device can be modified by the addition of an oxy-chlorine anion barrier. Specifically, the device contemplated herein comprises a chamber comprising an oxy-chlorine anion barrier, wherein the device has an inlet port for supplying a chlorine dioxide solution into the chamber and an outlet port for removing chlorine dioxide solution and an opening covered by the oxy-chlorine anion barrier. The chamber is designed to form a tight substantially leak-proof seal with the tissue surrounding an infected area, wherein the opening is proximal to the infected area. The oxy-chlorine anion barrier is interposed between the infected area and the chamber opening. The chlorine dioxide solution containing oxy-chlorine anions is introduced into the chamber, and chlorine dioxide passes through the oxy-chlorine anion barrier covering the opening and thereby contacting the infected area, while the passage of oxy-chlorine anions through the barrier is limited to substantially non-cytotoxic and/or substantially non-irritating levels. Exemplary materials useful as an oxy-chlorine anion barrier are described elsewhere herein.

5. Dose and Duration

The amount of the chlorine dioxide delivered by the composition comprising a chorine dioxide source varies within wide limits and can be adjusted to the individual requirements in each particular case. The amount depends on the condition treated, the general state of health of the recipient, the number and frequency of administrations and other variables known to those of skill in the art. Accordingly, the amount of chlorine dioxide to be delivered to a tissue (i.e., an efficacious amount) will relate to the result intended from the application of chlorine dioxide to the tissue. The skilled artisan can readily determine the appropriate amount or amount range of chlorine dioxide to be efficacious for a given use. Generally, useful amounts comprise, for example, from about 1 to about 2000 ppm chlorine dioxide, at least about 1 to about 1000 ppm or at least about 20 to about 400 ppm. In some embodiments, the chlorine dioxide is present in the composition in at least about 5 ppm, at least about 20 ppm, or at least about 30 ppm. Typically, the amount of chlorine dioxide can range to about 1000 ppm, up to about 700 ppm, up to about 500 ppm and up to about 200 ppm. In one embodiment, the composition comprises about 30 to about 100 ppm chlorine dioxide. In some embodiments, a useful dose range can be from about 2.5 mg chlorine dioxide per area of contact (in square meters) to about 500 mg/m$^2$ chlorine dioxide. Doses of at least about 10 mg/m$^2$, at least about 15 mg/m$^2$ and at least about 20 mg/m$^2$ can also be useful.

The duration of contact with the tissue to obtain efficacy can be readily determined by the skilled artisan in view of the teachings herein and the knowledge in the art. The duration of contact will be influenced, for instance, by the type of infection, the presence or absence of biofilm, the tissue type, whether treatment is therapeutic or prophylactic, and the formulation of the chlorine dioxide composition (e.g, liquid or gel or a slow-release formulation). Advantageously, even after prolonged contact, the composition does not substantially irritate mucosal or dermal tissue. Similarly, substantially contiguous iterations of contact with fresh specimens do not substantially irritate mucosal or dermal tissue. Generally, duration of contact ranges from seconds to minutes to hours to days. In some embodiments, the duration of contact can be at least about 60 seconds, at least about 1, 2, 3, 4, or 5 minutes, at least about 6, 7, 8, 9, or 10 minutes, or at least about 11, 12, 13, 14, or 15 minutes. In some embodiments, contact duration can range up to 16, 17, 18, 19, or 20 minutes, further up to 21, 22, 23, 24, 25, 26, 27, 28, 29, or 30 minutes, and further up to about 35, 40, 45, 50, 55, or 60 minutes or longer in some circumstances. In certain embodiments, duration of contact ranges between about 1 and about 60 minutes, from about 5 minutes to about 30 minutes, or from about 10 to about 20 minutes. In some embodiments, duration of contact for a treatment is about 15 minutes. In some embodiments, the duration of contact ranges from at least about one (1) hour to about 72 hours, from at least about 8 hours to about 48 hours, or from at least about 12 hours to about 36 hours. In certain embodiments, duration of contact ranges from about 1 hour to about 6 hours, or from about 1.5 hours to about 4 hours.

Dosage of chlorine dioxide can be expressed in terms of concentration of chlorine dioxide (in parts-per-million) times the duration (in minutes) of tissue contact with the chlorine dioxide, with the unit of ppm-min. Dosage refers to a single treatment. The concentration of chlorine dioxide is with respect to the composition used in the single treatment. The single treatment can comprise a single contacting step or multiple contacting steps (e.g., substantially contiguous iterations). In some embodiments, dosage in terms of ppm-minute can range from about 100 ppm-minutes to about 10,000 ppm-minutes, or from about 200 ppm-minutes to about 5000 ppm-minutes. In embodiments where the method is practiced on an infection comprising a biofilm, dosage of at least about 200 ppm-minutes is useful. These ranges are appropriate for applications in "clean" systems, e.g., application having little or no organic material other than the pathogens. In embodiments for treating infected biological tissue comprising a protein-rich environment, such as wound exudate, these ranges are suitable target ranges for the actual dosage administered, as discussed below, to achieve a significant reduction in bacteria or other pathogens.

The amount of chlorine dioxide in a composition can decrease due to the presence of organic material, such as protein. For instance, wound beds are protein-rich environments that comprise blood serum. Actual dosage of chlorine dioxide therefore varies depending on the amount of wound fluid, the percent blood serum in the wound fluid and the amount of chlorine dioxide in the treatment composition. An actual dosage is therefore the dosage corrected for the loss of chlorine dioxide due to the presence of blood serum in a wound bed. As shown herein, one can estimate the actual chlorine dioxide concentration in a wound environment as a function of time, and thereby estimate an actual dosage during a chlorine dioxide treatment in the presence of wound fluid. The actual dosage estimate is calculated by determining the $ClO_2$ concentration in solution as a function of time, and then integrating that equation over the contact time of treatment. The details are as follows.

First, one calculates the starting weight ratio of blood serum to $ClO_2$ ($BS/ClO_2$). To do that, one has to estimate the estimate milligrams of blood serum BS in the wound by estimating the weight of wound fluid WF in the wound (in mg). It is assumed that wound fluid generally contains about 5% by weight blood serum. Therefore, to estimate the milligrams of blood serum BS in the wound, WF (in mg) is multiplied by 5%:

$$BS \text{ (in mg)} = WF \text{ (in mg)} \times 5\% \quad (1)$$

To calculate the weight of $ClO_2$, one must know the amount in mg of treatment composition Mt that will be applied to the wound, and the ppm $ClO_2$ in that treatment material. The mass of $ClO_2$ in the treatment composition is then calculated using the equation below:

$$\text{mg } ClO_2 = Mt \text{ (mg)} \times [ClO_2]/1{,}000{,}000 \quad (2)$$

where: Mt=mass of the treatment composition in mg, and $[ClO_2]$=$ClO_2$ concentration in ppm in the treatment composition. The mg of blood serum in the wound is divided by the mg of $ClO_2$ in the treatment composition to obtain the $BS/ClO_2$ ratio:

$$BS/ClO_2 = BS \text{ (in mg)}/\text{mg } ClO_2 \quad (3)$$

As shown herein, the decay rate K2 of chlorine dioxide as a function of the ratio of the blood serum to the mass of $ClO_2$ in the treatment composition is estimated by the equation:

$$K2 = -0.00927(BS/ClO_2) + 1 \quad (4)$$

Therefore, K2 is estimated by plugging in the result of equation 3 into equation 4. K2 is then plugged into the equation:

$$Ct = Co \times t^{K2} \quad (5)$$

where Ct=the concentration of $ClO_2$ as a function of time; Co=the initial $ClO_2$ concentration in ppm; and t=time in minutes. This function is then integrated as a function of time over the treatment time of the wound. The result of the integration is an estimate of the actual dosage in the wound. This estimate and the minimum efficacious dose in a clean system (discussed above) can enable a clinician to chose an appropriate treatment composition regarding the chlorine dioxide concentration in the treatment composition. In some embodiments, the method comprises treatment of an actual dosage of about 200 ppm-min to about 15,000 ppm-min, about 500 ppm-min to about 5000 ppm-min, or about 750 ppm-min to about 2000 ppm-min.

EXAMPLES

The compositions and methods of use are further described in detail by reference to the following experimental examples. These examples are provided for purposes of illustration only, and are not intended to be limiting unless otherwise specified. Thus, the compositions, methods of use, and systems should in no way be construed as being limited to the following examples, but rather, should be construed to encompass any and all variations which become evident as a result of the teaching provided herein.

Example 1

Chlorine Dioxide Efficacy Against Biofilm

Chlorine dioxide treatment involves exposing micro-organisms to chlorine dioxide for a period of time. Treatment conditions, often called the dosage of chlorine dioxide, can be determined by calculating the integral of the chlorine dioxide concentration as a function of time, C(t), over the treatment time of use:

$$\text{Dose} = \int_0^T C(t)dt \quad (6)$$

In systems where the chlorine dioxide concentration is generally constant over the treatment time (e.g., varies by less than ±10% relative) or varies linearly over the treatment time, an average chlorine dioxide concentration can be calculated by averaging the starting and ending concentrations and then multiplying that average chlorine dioxide concentration during an exposure period by the time of exposure (Average Concentration×time):

$$\frac{(Ct + Co)}{2} \times t \quad (7)$$

where Ct is the ending $ClO_2$ concentration at time t, and Co is the initial chlorine dioxide concentration. Dosage is commonly given in units of ppm-minutes.

A series of experiments were conducted to estimate the dosage of chlorine dioxide needed to kill bacterial biofilms consisting of *Pseudomonas aeruginosa* (PA), methicillin resistant *Staphylococcus aureus* (MRSA), or a combination of both.

Bacterial biofilms were grown for between 7 and 10 days on non-porous ceramic disks in a spinning disk biofilm reactor. The reactors were inoculated with PA, MRSA, or a mixture of MRSA and PA bacteria to produce PA, MRSA, or mixed PA/MRSA biofilms respectively.

Chlorine dioxide solutions were produced at different nominal concentrations using ASEPTROL® S-Tab10 tablets, and the exact concentrations were then measured using a Hach Model 2400 UV/Vis spectrophotometer in accordance with the manufacturer's instructions. Pairs of biofilm-containing disks were immersed for different times in solutions of different chlorine dioxide concentrations, neutralized with dilute sodium thiosulfate solution, and then plated to determine the number of surviving bacteria on each disk. Two untreated disks were also exposed to neutralizing solution and plated to determine the starting bacterial counts. In all tests, the baseline bacterial counts were in the range of $10^7$ to $10^{7.5}$ colony-forming units per disk (cfu/disk). A one log reduction refers to reducing the cfu/disk by one order of magnitude, e.g., a reduction from $10^{7.1}$ cfu/disk to $10^{6.1}$ cfu/disk. Accordingly, a substantially complete kill is achieved in the example if the log reduction of bacteria is about 7 to 7.5.

Table 1 summarizes the test conditions used in the different experiments. The results are presented in terms of log reduction of the different bacterial organisms. In the case of mixed PA/MRSA biofilms, results are given as total bacteria. The data are also shown in FIG. 1.

TABLE 1

| Sample # | Organism | Exposure Time (minutes) | ClO2 Concentration (ppm) | Conc × Time (ppm-min) | Log Reduction in Organism Count |
|---|---|---|---|---|---|
| 1 | MRSA | 1.0 | 208 | 208 | 5.5 |
| 2 | MRSA | 5.0 | 204 | 1020 | 7.1 |
| 3 | MRSA | 10.0 | 45 | 450 | 5.5 |
| 3 | MRSA | 30.0 | 40 | 1200 | 5.1 |
| 4 | MRSA | 30.0 | 175 | 5250 | 7.1 |
| 6 | PA | 0.5 | 200 | 100 | 5.9 |
| 7 | PA | 5.0 | 43 | 215 | 5.7 |
| 8 | PA | 5.0 | 187 | 935 | 7.5 |
| 9 | PA | 10.0 | 37 | 370 | 7.5 |
| 10 | PA | 50.0 | 35 | 1750 | 7.5 |
| 11 | PA | 50.0 | 166 | 8300 | 7.5 |
| 12 | MRSA + PA | 10.0 | 52 | 520 | 5.5 |
| 13 | MRSA + PA | 30.0 | 52 | 1560 | 7.4 |
| 14 | MRSA + PA | 1.0 | 181 | 181 | 5.1 |
| 15 | MRSA + PA | 5.0 | 160 | 800 | 7.4 |
| 16 | MRSA + PA | 30.0 | 160 | 4800 | 7.4 |

These data show that complete kill of either a PA biofilm, a MRSA biofilm or a mixed PA/MRSA biofilm was achieved with a dosage of between about 400 and 1000 ppm-minutes (see Samples 2, 9 and 15). A PA biofilm appeared slightly easier to kill than a MRSA biofilm, but the difference is small. A kill of about 5 orders of magnitude (i.e., 5 log) can be achieved at a dosage of greater than about 200 ppm-min (see Samples 1, 7, and 12). These data demonstrate that chlorine dioxide has great potency for disrupting and eradicating biofilms using readily achievable dosages, which are substantially non-cytotoxic and/or non-irritating to biological tissue.

Example 2

Chlorine Dioxide Loss in Protein-Rich Solution

Oxidizing biocides can react with and be destroyed by organic material, such as proteins. While chlorine dioxide is generally recognized as a relative unreactive oxidizing biocide, chlorine dioxide can be consumed in the organic-rich treatment environment of a wound. Blood serum is a protein-rich material and is a particularly reactive component of wounds.

A series of experiments were conducted to estimate and quantify the effect of blood serum on chlorine dioxide concentration. Solutions of chlorine dioxide and fetal blood serum (FBS) were prepared at different concentrations of chlorine dioxide and FBS, and the chlorine dioxide concentration was tracked using a Spectral Physics UV/Visible spectrophotometer with a direct insertion probe (1 mm path length).

The initial chlorine dioxide concentration was measured using a Hach Model 2400 UV/Vis spectrophotometer. A UV/Vis scan was then measured over the wavelength range of about 200 to 600 nm using the direct insertion probe, and this was used to calculate the initial absorbance of the solution. FBS was then added, and UV/Vis scans were run periodically thereafter. The area of the chlorine dioxide absorbance peak was calculated for each scan, and the relative chlorine dioxide concentration at each time was calculated by dividing the area at each time point by the peak area of the initial scan (prior to FBS addition).

Figure 2:
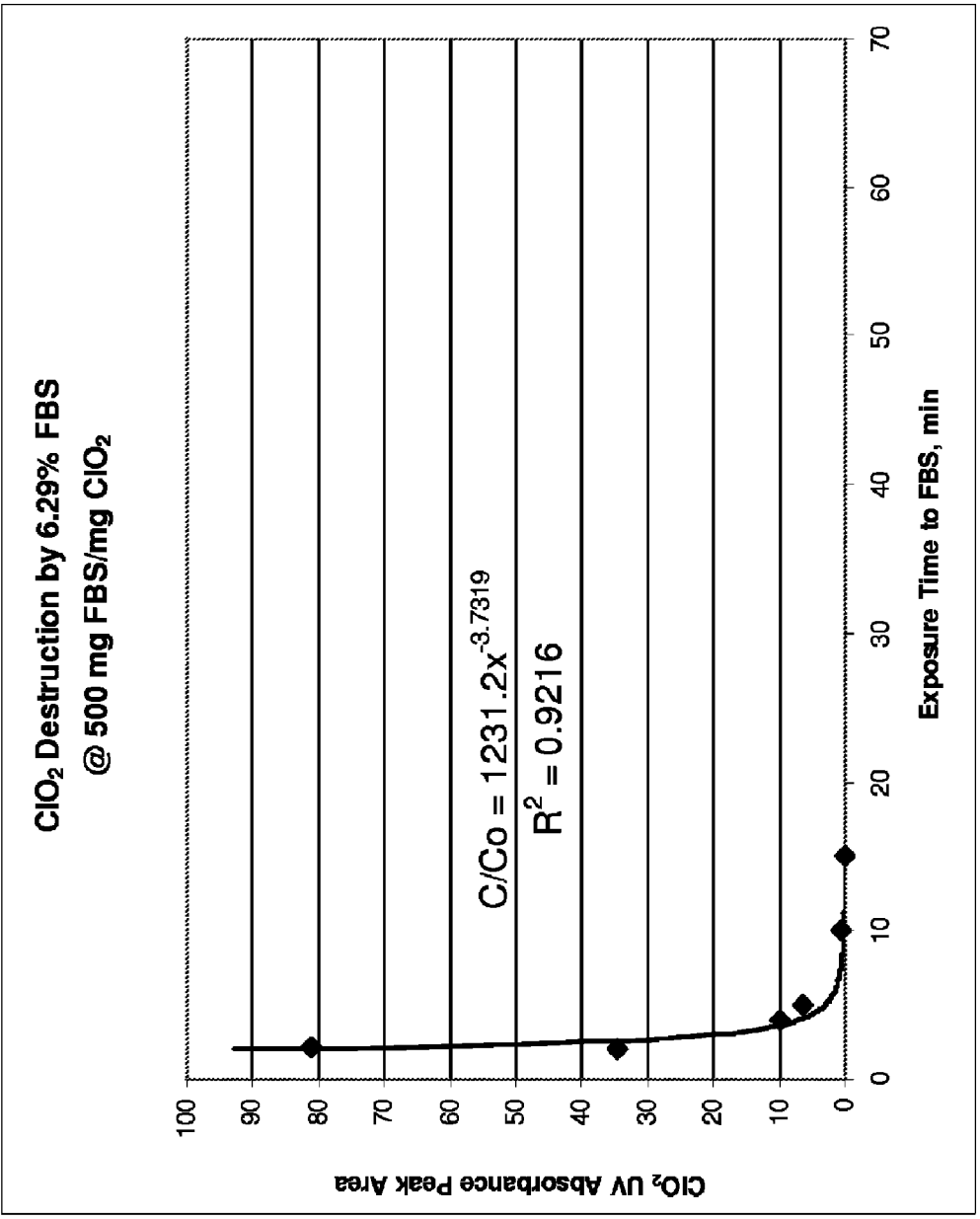
FIG. 2 is a graph depicting representative data for decrease in chlorine dioxide ($ClO_2$) as a function of time in a protein-rich environment. The data depicted were measured for a solution containing 6.29% by wt. fetal blood serum (FBS) and having an initial weight ratio (mg/mg) of FBS/$ClO_2$ of nominally 500.

Relative chlorine dioxide concentration was plotted versus time for each set of chlorine dioxide and FBS concentrations. The curves were well fit by regression to a function of the form:

$$Ct/Co = t^{K2} \quad (8)$$

where Ct is the $ClO_2$ concentration at time t, and Co is the initial chlorine dioxide concentration. Data for a solution containing 6.29 wt. % FBS and having an initial FBS/$ClO_2$ weight ratio of nominally 500 (mg/mg) are depicted in FIG. 2. The exponent K2 in the equation is an estimate of the decay rate of chlorine dioxide in the FBS solution. The weight ratio of FBS to chlorine dioxide was calculated by dividing the mass of FBS added to the solution by the mass of chlorine dioxide in the solution.

Figure 3:
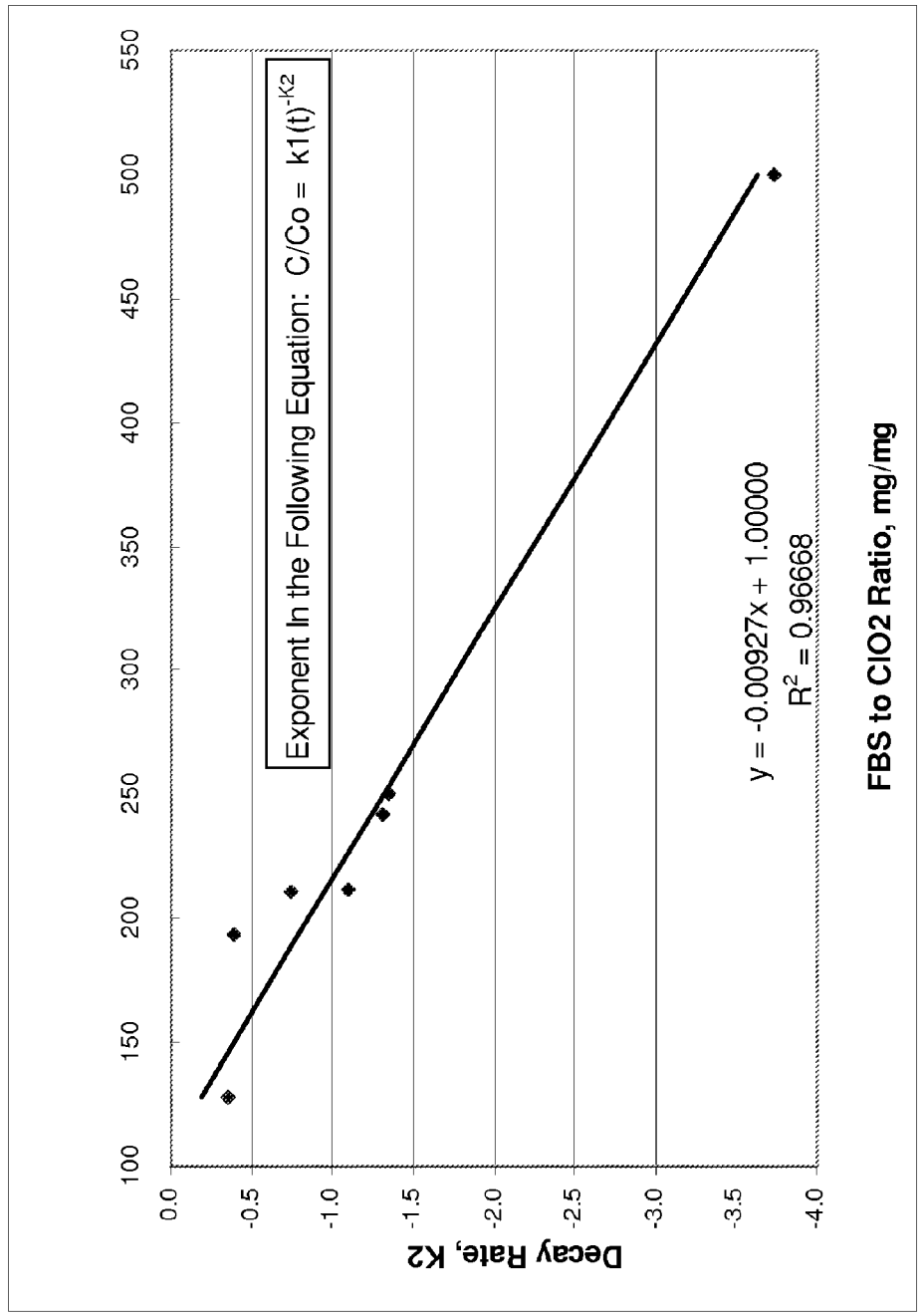
FIG. 3 is a graph of chlorine dioxide decay rates as a function of the initial weight (mg/mg) ratio of fetal bovine serum (FBS) to chlorine dioxide.

The decay rates for the different solution concentrations were then plotted versus the initial mass ratio of FBS/$ClO_2$ for each system. These results are depicted in FIG. 3. FIG. 3 shows that the decay rate K2 decreases linearly with the initial FBS/$ClO_2$ ratio, and fits the equation:

$$K2 = -0.00927(FBS/ClO_2) + 1 \quad (9)$$

Using this relationship, it is possible to estimate the actual chlorine dioxide concentration in a wound environment as a function of time, and thereby estimate an actual dose during chlorine dioxide treatment in the presence of wound fluid. By targeting an actual dose of greater than about 500 ppm-min, one can expect nearly complete kill of accessible biofilm in the wound. An actual dose of greater than about 200 ppm-min should yield greater than about 5 log kill of accessible biofilm.

Example 3

Chlorine Dioxide Efficacy Against Biofilm in Protein-Rich Environment

A series of experiments were conducted to determine the effect of FBS on the kill of PA, MRSA and mixture PA/MRSA biofilms. Biofilms were grown as described in Example 1. Disks were immersed in 25 ml of FBS solution at double the target FBS concentration, and to that was added 25 ml of chlorine dioxide solution at double the target chlorine dioxide concentration. After the desired contact time, disks were removed from the treatment solutions, neutralized, and plated as described above.

Treatment conditions and results are shown in Table 2. Dosage is given both as the nominal dose based upon the initial chlorine dioxide concentration, and the actual dosage as estimated from the initial chlorine dioxide concentration and the decay relationships described above.

TABLE 2

| 1 Sample # | 2 Organism | 3 Exposure Time (minutes) | 4 Initial ClO$_2$ Concentration (ppm) | 5 Nominal Dosage, Conc × Time (ppm-min) | 6 Log Reduction in Organism Count | 7 mg FBS/ mg ClO$_2$ | 8 Decay rate, K2 | 9 Final ClO$_2$ Concentration, ppm | 10 Average ClO$_2$ Concentration, ppm | 11 Corrected Dosage, C × t, ppm-min |
|---|---|---|---|---|---|---|---|---|---|---|
| 17 | MRSA + PA | 15.0 | 191 | 2865 | 8.2 | 131 | −0.2134 | 107 | 149 | 2236 |
| 18 | MRSA + PA | 40.0 | 191 | 7640 | 8.2 | 131 | −0.2134 | 87 | 139 | 5559 |
| 19 | MRSA + PA | 15.0 | 240 | 3600 | 8.2 | 104 | 0.0344 | 240 | 240 | 3600 |
| 20 | MRSA + PA | 30.0 | 240 | 7200 | 8.2 | 104 | 0.0344 | 240 | 240 | 7200 |
| 21 | MRSA + PA | 60.0 | 240 | 14400 | 8.2 | 104 | 0.0344 | 240 | 240 | 14400 |
| 22 | MRSA | 15.0 | 191 | 2865 | 4.7 | 131 | −0.2134 | 107 | 149 | 2236 |
| 23 | MRSA | 40.0 | 191 | 7640 | 4.7 | 131 | −0.2134 | 87 | 139 | 5559 |
| 24 | MRSA | 15.0 | 240 | 3600 | 4.7 | 104 | 0.0344 | 240 | 240 | 3600 |
| 25 | MRSA | 30.0 | 240 | 7200 | 4.7 | 104 | 0.0344 | 240 | 240 | 7200 |
| 26 | MRSA | 60.0 | 240 | 14400 | 4.7 | 104 | 0.0344 | 240 | 240 | 14400 |
| 27 | PA | 15.0 | 191 | 2865 | 7.1 | 131 | −0.2134 | 107 | 149 | 2236 |
| 28 | PA | 40.0 | 191 | 7640 | 7.1 | 131 | −0.2134 | 87 | 139 | 5559 |
| 29 | PA | 15.0 | 240 | 3600 | 7.1 | 104 | 0.0344 | 240 | 240 | 3600 |
| 30 | PA | 30.0 | 240 | 7200 | 7.1 | 104 | 0.0344 | 240 | 240 | 7200 |
| 31 | PA | 60.0 | 240 | 14400 | 7.1 | 104 | 0.0344 | 240 | 240 | 14400 |

Figure 4:
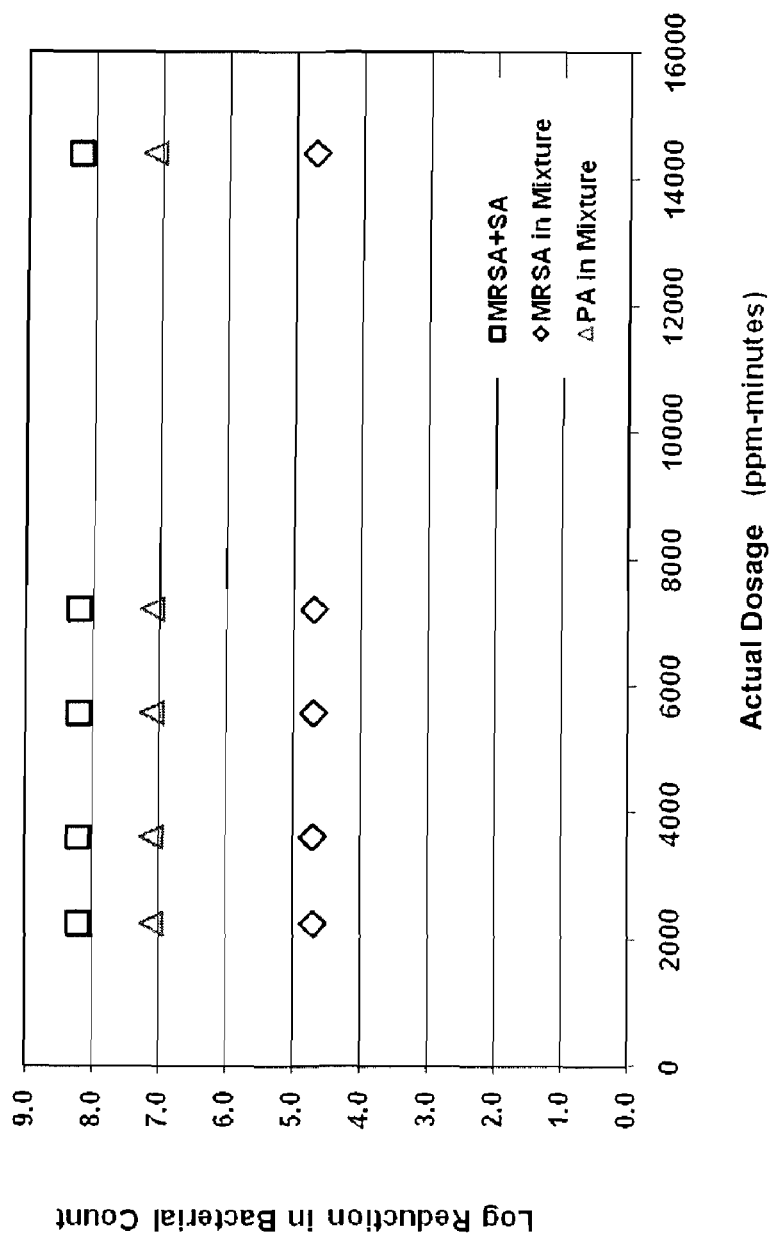
FIG. 4 is a graph depicting the reduction in log bacteria in various biofilms as a function of corrected chlorine dioxide dosage. Chlorine dioxide dosage was corrected to reflect the chlorine dioxide consumption attributable to reaction with organic material (e.g., proteins) other than the bacteria.
Figure 5:
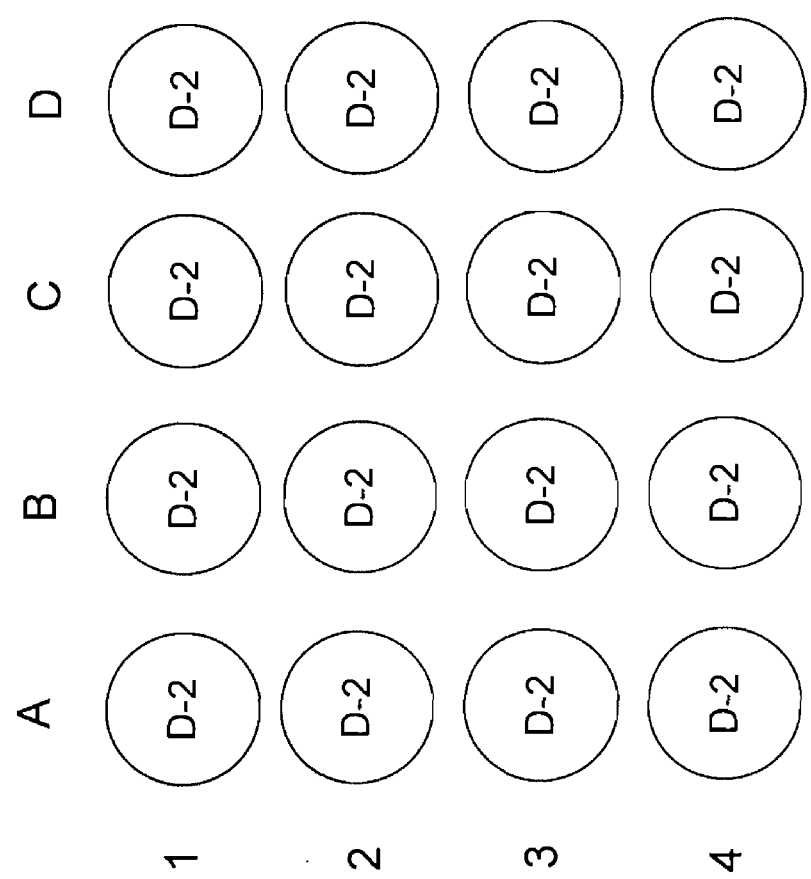
FIG. 5 is a schematic representation of the wound placement in an assessment of various delivery methods for contacting a wound with chlorine dioxide. D-2 indicates that the wound was biopsied on Day 2.

Columns 3-6 are measured data; columns 7-11 are calculated data. For K2 having a positive sign (such as Samples 20-21), it was assumed that there was insufficient FBS present to cause a material loss of chlorine dioxide. Therefore, for such samples, it was assumed that chlorine dioxide was unchanged over the time of the experiment FIG. 4 is a graph of the results. These data demonstrate that, like the bacterial kill results in a "clean system" (free of FBS; see Example 1), bacterial kill in a "dirty system" (e.g., rich in organic matter) can be predicted from the corrected FBS concentration. Specifically, corrected dose rates of about 2000 ppm-min and higher resulted in complete kill for each type of biofilm tested.

Example 4

Chlorine Dioxide Delivery Methods for Wound Treatment

This study was designed to generate initial data for the assessment of various delivery methods of ClO$_2$ into infected wounds and to ascertain the drug's effect on microbial bioburden and wound healing.

The test animal was a pig (n=1). Pigs are commonly used as models for wound healing in part because pig skin shares many characteristics with human skin. The porcine model is considered to be an excellent tool for the evaluation of candidate agents intended for use in human wounds.

The pig was housed in accordance with "Guide for the Care and Use of Laboratory Animals DHEW" (NIH). The pig was fed fresh porcine diet daily and water was available ad libitum. The pig was housed in a temperature-controlled animal room, having a 12-hour light/dark cycle. The room was kept clean and free of vermin.

On Day 0, the pig was anesthetized and sixteen (15) full-thickness wounds (eight per side) were created using a custom designed 2-cm trephine. Each wound was 2-cm in diameter. An epinephrine solution (1:10,000 dilution) was applied to the wounds on gauze sponges until hemostasis was complete (approximately 10 minutes). Each wound was then infected with a bacterial inoculum.

Three different bacteria, *Pseudomonas aeruginosa*, *Fusobacterium* sp., and coagulase-negative Staphylococci (CNS), were cultured and used to prepare inoculums for the wounds. On the morning of surgery, the bacterial cultures were washed with sterile saline and resuspended in saline to a final density of approximately $10^7$ CFU/mL. This bacterial suspension was used to inoculate each wound.

Wounds were dressed with sterile Telfa gauze, and the infections allowed to mature to establish a bacterial biofilm condition. Telfa dressings were moistened with saline; the excess saline was removed by squeezing the Telfa dressings. The dressing was then secured in place with Transpore tape (3M, St. Paul, Minn.). As a secondary dressing, a blue absorbent pad was used to cover all of the wounds. The absorbent layer of the blue pad was placed against the skin for the first few days. If wounds looked too dry, the blue pad was changed with the occlusive side against the skin. A layer of a layer of elastic bandage was wrapped over the blue pad to prevent movement of the dressings underneath. All wound dressing were changed on Day 1.

On Day 2, wounds were treated with a chlorine dioxide composition using different delivery methods. In brief, wounds A2-A4 were treated with continuous irrigation. Treatment for wounds B2-B4 and C2-C4 was multiple, substantially contiguous episodes of contact with a substantially non-cytotoxic chlorine dioxide gel composition. Wounds D2-D4 were treated with intermittent irrigation using a manual irrigation device. A1, B1 and D1 were controls and were not treated with chlorine dioxide. C1 was manually treated with a chlorine dioxide solution.

Wounds A2-A4: Each wound was individually covered with an irrigation device, each having an inlet port to supply a chlorine dioxide solution and an outlet port for egress of the chlorine dioxide solution. The inlet ports were connected by flexible tubing to the outlet of a three-head, adjustable speed pump. The inlets of the pump were connected to the fluid supply source containing a 400 ppm chlorine dioxide solution. A second set of flexible tubing was connected to the outlet ports, which drained into a common waste container. The chlorine dioxide solution was not re-circulated.

The pump was activated to achieve an initial flow rate of approximately 80-82 mL/min through each of the three irrigation chambers. Chlorine dioxide concentrations were measured at the outlets using a UV spectrophotometer. The flow was adjusted as required until the outlet concentrations were no less than 85% of the source concentrations.

Wounds B2-B4: A 400 ppm chlorine dioxide gel comprising 2.83 wt % NaCMC was applied to each wound in 8 separate, contiguous applications. Each application was about 2.5 ml of the gel. For each application, after the wound was contacted with the gel, the wound was covered and remained covered for 12 minutes. The dressing was removed and the gel was rinsed off the wound using saline (taking ~3 minutes). Thus, the 8 separate applications were administered over a period of two hours. A masterbatch of the 400 ppm chlorine dioxide gel was prepared using a concentrated NaCMC base gel and a concentrated freshly-prepared solution of chlorine dioxide (prepared using an ASEPTROL S-Tab2 tablet). The solutions were mixed using syringes connected with Luerlok union. The eight aliquots were taken from this masterbatch for the separate applications.

Wounds C2-C4: These wounds were treated the same as wounds B2-B4, using a 400 ppm chlorine dioxide gel comprising 1.5. wt. % HPMC. A masterbatch of the 400 ppm chlorine dioxide gel was prepared as described above for the NaCMC gel; the eight aliquots were taken from the masterbatch for the separate applications.

Wounds D2-D4: Each wound was covered with a manual irrigation device having syringes. A masterbatch solution of 400 ppm chlorine dioxide was prepared at the start of the treatments. For each application, a fresh specimen (20 ml) was removed, mixed for 1 minute, then applied to the wound via syringe and left to stand for 9 minutes. There were a total of 12 treatments administered over a period of two hours.

Wound C1: Using a syringe, 50 ml of 400 ppm chlorine dioxide solution was administered every 5 minutes. Thus, there were 24-50 ml applications over a period of two hours. The solution used to irrigate the wound was collected after irrigation, but was not reused.

Wounds A1, B1 and D1 were not treated. To keep the wounds moist, each wound was covered with an occlusive dressing until it was time to biopsy the wound.

After treatment, each wound was biopsied. The number of bacteria in each biopsy sample was assessed as follows. Biopsy tissue sample was placed into a pre-weighed vessel containing phosphate buffered saline, and the weight of tissue determined. The tissue sample was then homogenized and serially diluted. The serial dilutions were Drop-Plated and incubated to determine the bacterial counts. One set of samples were plated on Tryptic Soy Agar (TSA) to determine the total bacterial counts in the biopsy specimen. Another set of samples was plated on Mannitol Salts Agar (MSA) to determine the number of staphylococci present in the biopsy specimen. A third set of samples was plated on *Pseudomonas* Isolation Agar (PIA) to determine the number of *P. aeruginosa* present in the biopsy specimen. Bacterial counts are expressed as $\log_{10}$ (CFU/g).

Figure 6:
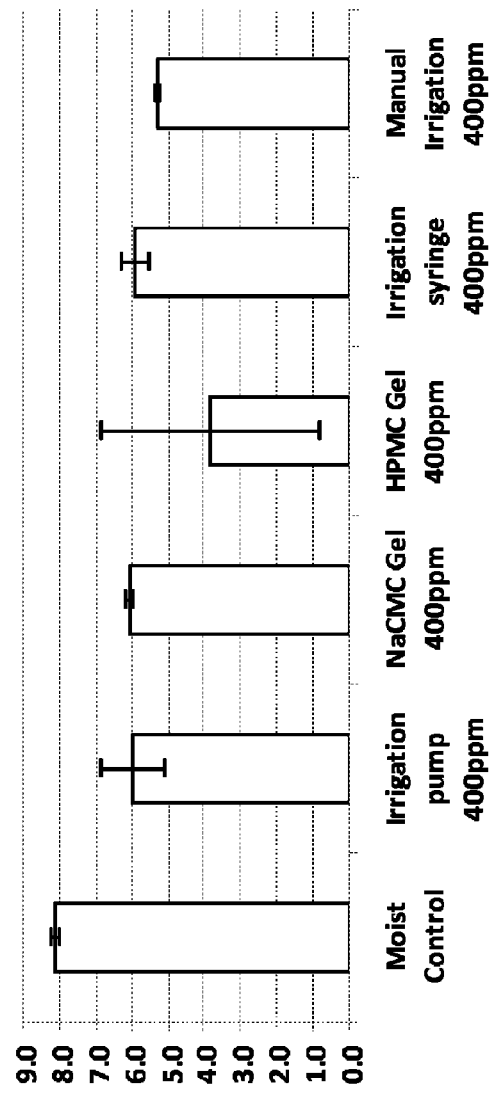
FIG. 6 is a bar graph depicting the total bacteria log in wounds after different delivery methods. The y-axis is log total bacteria in colony-forming units (CFUs) per gram tissue. Moist control: data for wounds A1, B1, and D1. Irrigation pump: data for wounds A2-A4. NaCMC gel: data for wounds B2-B4. HPMC gel: data for wounds C2-C4. Irrigation syringe: data for wounds D2-D4. Manual irrigation: data for wound C1. NaCMC=sodium carboxymethylcellulose. HPMC=hydroxypropyl methylcellulose.

The data for total bacteria count is depicted in FIG. 6. The moist controls averaged slightly over 8 log of total bacteria per gram tissue. The treated wounds all averaged about 6 or less log total bacteria. The HPMC gel data set (wounds X2-X4) contained one zero count sample, which accounts for the large error shown for this data in FIG. 6. Since the MSA and PIA plates for this same sample both showed positive microbial cultures, this zero result is likely the result of a sample processing error. Without this zero data included, the average Log CFUs for this sample was 5.8, in line with the other treatments. The data in FIG. 6 demonstrate that for all delivery methods, a total bacteria reduction in the range of 2-4 logs was achieved (2-3 logs if the zero data for the HPMC data set is excluded).

Figure 7:
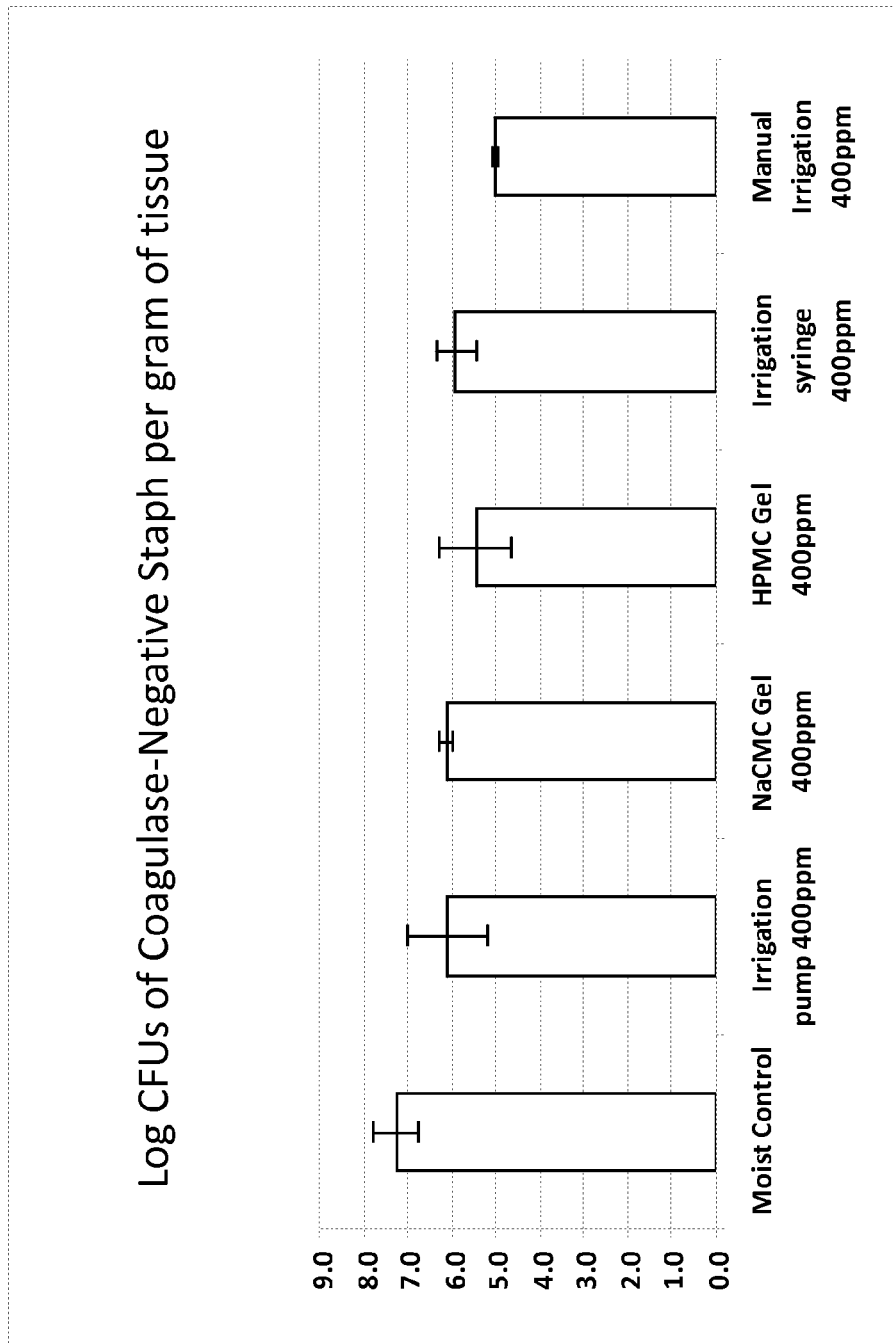
FIG. 7 is a bar graph depicting the total log of coagulase-negative Staphylococci in wounds after different delivery methods. The y-axis is log coagulase-negative Staph in CFUs per gram tissue. Moist control: data for wounds A1, B1, and D1. Irrigation pump: data for wounds A2-A4. NaCMC gel: data for wounds B2-B4. HPMC gel: data for wounds C2-C4. Irrigation syringe: data for wounds D2-D4. Manual irrigation: data for wound C1.

Data for coagulase-negative Staph are depicted in FIG. 7. The moist controls averaged over 7 log of total coagulase-negative Staph per gram tissue. The treated wounds all averaged about 6 or less log coagulase-negative Staph per gram tissue. The data in FIG. 7 demonstrate that for all delivery methods, a reduction of coagulase-negative Staph in the range of 1-2 logs was achieved.

Figure 8:
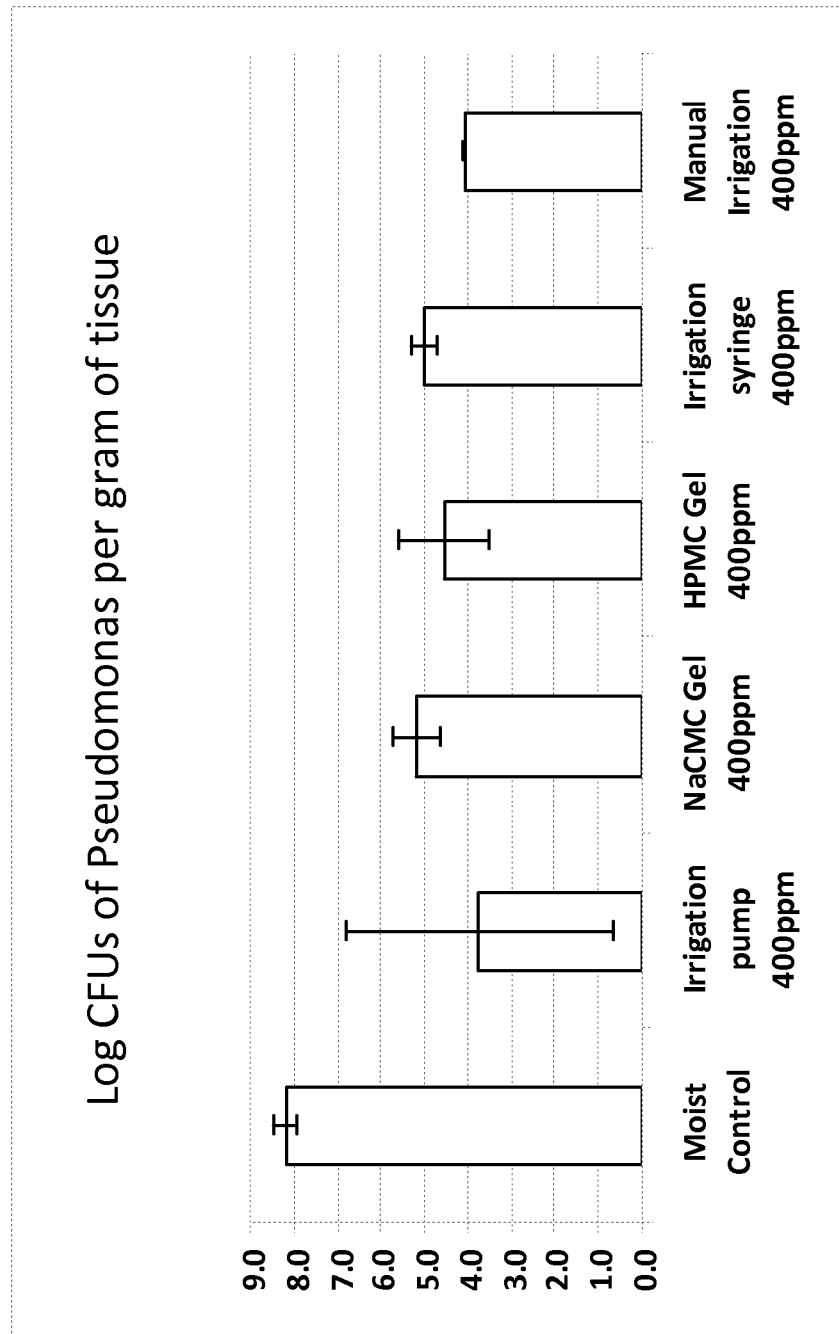
FIG. 8 is a bar graph depicting the total log of *Pseudomonas* in wounds after different delivery methods. The y-axis is log *Pseudomonas* in CFUs per gram tissue. Moist control: data for wounds A1, B1, and D1. Irrigation pump: data for wounds A2-A4. NaCMC gel: data for wounds B2-B4. HPMC gel: data for wounds C2-C4. Irrigation syringe: data for wounds D2-D4. Manual irrigation: data for wound C1.

Data for *Pseudomonas* are depicted in FIG. 8. The moist controls averaged over 8 log of total *Pseudomonas* per gram tissue. The treated wounds all averaged slightly more than 5 log or less log *Pseudomonas* per gram tissue. The data in FIG. 8 demonstrate that for all delivery methods, a reduction of *Pseudomonas* in the range of 3-5 logs was achieved.

The results of this example indicate that the improved irrigation methods used in this study and also the application of chlorine dioxide in a gel formulation moderately lowered the levels of *Staphylococcus aureus*. Chlorine dioxide was shown to be potent against *Pseudomonas*, with log reductions of 3 or greater. Additionally, using the improved drug-delivery methods in this study, a 1-2 log reduction in both *Staph* and total bacterial levels was also achieved.

Example 5

Efficacy of Chlorine Dioxide Composition with Sonication in Pig Model

An experiment was performed to assess the efficacy of a combination therapy of chlorine dioxide administration and sonication on bacterial levels in wounds. The animal model was a pig. Sixteen wounds were introduced and inoculated with bacteria as described in Example 6. On Day 2, treatment was administered. There were control wounds that were not treated with either chlorine dioxide or ultrasound. Test wounds were treated with ultrasonic energy for 4 minutes, using a frequency of about 20 kHz, a 40% duty cycle and a range of power intensities up to 3.5 W/cm$^2$; each test wound received a total of three sonication treatments. Test wounds were treated with a 400 ppm chlorine dioxide solution applied to each wound in 8 separate, contiguous applications of 15 minutes duration each (total of 120 minutes of exposure to 400 ppm chlorine dioxide) and each application used a fresh specimen of the solution. Each treated wound received a total of three×4 minute sonication over the course of the 2 hours of chlorine dioxide treatment.

Wounds were biopsied after treatment as described in Example 4. Bacterial counts were found to decrease significantly (multiple log reductions) in the test wounds as a function of the power intensity. At 3.5 W/cm$^2$, a substantially complete log kill was achieved.

Example 6

Prophetic-Chlorine Dioxide Efficacy in Pig Model with Sonication

An experiment will be performed to further assess the efficacy of a combination therapy of chlorine dioxide administration and sonication on bacterial levels in wounds as a function of different parameters. The animal model will be a pig. Sixteen wounds will be introduced and inoculated with bacteria as described in Example 4. On Day 2, treatment will be administered. There will be control wounds that are not treated with either chlorine dioxide or ultrasound, and control wounds treated only with ultrasound or only the chlorine dioxide composition. Test wounds will be designed to study efficacy as a function of different parameters, including frequency, power intensity and duty cycle of ultrasonic energy, duration of treatment and formulation of the composition comprising chlorine dioxide (e.g., liquid, gel, or slow-release). Wounds will be biopsied after treatment as described in Example 4. Further tests can be pursued using additional test animals, if necessary.

Based on the result of Example 5, the use of ultrasound is expected to improve chlorine dioxide penetration into the tissue and therefore improve the log reduction of bacteria in a statistically significant amount, e.g., by at least about 0.5 log and preferably, by at least about 1 or 2 logs, in comparison to the use of chlorine dioxide composition alone.

Example 7

Tooth Whitening with Multiple, Contiguous Applications

This study was designed to assess the efficacy on tooth whitening of two different regimens of multiple, contiguous applications of a 200 ppm chlorine dioxide gel.

Five human extracted teeth (molars) were used in this study. Each tooth was sectioned twice: first at the tooth's cemento-enamel junction to remove the root portion of the tooth; then sectioned mesio-distally to separate the tooth into two, separate buccal and lingual halves. The buccal and lingual tooth segments thereby revealed exposed axial and gingival portions or planes of dentin (connected by an axio-pulpal or axio-gingival lineangle of approximately 90°) in each sectioned tooth segment. The sectioned teeth were then stained in concentrated black tea (cooled to room temperature after brewing) until each tooth accumulated enough stain to be visually graded as "C4" (but no lighter than "A4") per the Vita Classic Shade Vision Guide.

After staining, the cut sides of each tooth were sealed with an acrylic polymer (i.e. acrylic-based nail polish). The tooth was then "split" or functionally "divided" into a left and right sides (the tooth was not physically split). To create "dividing line," a narrow channel was first created down the center of the tooth (running from the occlusal to the gingival or cervical portion of the tooth) using a narrow tungsten carbide or diamond tip dental bur, thereby creating an approximately 0.5 to 1.5-mm deep by 1 to 1.5-mm wide channel on either the buccal or lingual enamel surface of the tooth segment. The channel was etched carefully with a 34-40% phosphoric acid dental etching gel preparation (being careful to confine the gel only to the enamel within the prepared channel). The etching gel was then removed by water rinsing, the surface was dried, and a thin, narrow band of enamel-dentin adhesive was then applied carefully only to the enamel within the narrow channel. The material was allowed to dry in ambient air for 1 minute then carefully dried with a gentle stream of compressed air for an additional 10 seconds. The enamel-dentin adhesive was subsequently cured by exposure to a visible light dental curing unit using actinic blue light at an approximate peak wavelength of 470 nm for multiple, 20 second curing increments. In order to fill in the channel and gradually build a "wall" or barrier to separate the left and right half of the lingual surface of the tooth, a thin, narrow layer or band of composite resin dental restorative material was added in several steps and cured with the dental visible blue-light curing unit.

The wall that was built up on each tooth prevents whitening agent applied on the left side of the tooth to migrate into the whitening agent that was applied on the right side of the tooth, and visa versa. In this way, it is possible to compare two different treatment regimens on the same tooth, thereby minimizing the biological diversity among different teeth that may affect whitening efficacy.

Two treatment regimens were tested, both using a nominal 200 ppm chlorine dioxide gel comprising sodium carboxymethylcellulose (NaCMC). The actual concentration of chlorine dioxide was measured and found to be 155 ppm; pH of the composition was 5.0. The general treatment protocol is as follows. After mixing, the $ClO_2$ gel was drawn into a 60 ml plastic syringe. The 60 ml syringe was used to store the gel during the assay, and for dispensing gel into a 10 ml plastic syringe. The gel in the 10 ml syringe was then dispensed directly onto the tooth section enamel surfaces as follows. At time zero, about 1 to 1.5 ml gel was dispensed onto the enamel surface of each tooth segment attached to the glass microscope slide. The thickness of the resulting gel layer was about 1.5 to 3.0 mm in depth. After dispensing the gel onto the tooth segments, the glass slide was placed in a plastic zippered bag, containing small strips of wet paper towel within the bag to maintain 100% humidity in the bag. The paper towel strips were positioned to eliminate any contact of the plastic bag with the tooth and gel surfaces.

Upon conclusion of a contact epidose, the glass slide was removed from the plastic bag, and the gel was carefully removed with an extra soft bristle toothbrush and a gentle stream of running tap water. The tooth segments were then analyzed for shade, and the gel application procedure was repeated as designed until the experiment was concluded. The tested tooth segments were stored on the glass microscope slide in 100% humidity for later reference observation. Care was taken to keep the teeth hydrated throughout the experiment to avoid undue color artifact resulting from dehydration. The left side of each tooth was administered four separate, substantially contiguous applications, each with a contact length of 15 minutes in duration. The right side of each tooth was administered eight separate, substantially contiguous applications, each with a contact length of 7.5 minutes in duratio. Thus, both sides of the teeth were exposed to the chlorine dioxide composition for a total of 60 minutes, with a nominal dosage of 12,000 ppm-min.

Each application used a fresh specimen of chlorine dioxide gel composition. Tooth whitening was assessed visually using the Vita Classic Shade Vision Guide. Visual assessment by Vita Classical Shade Guide: Initial baseline shade and subsequent shade change was assessed by direct comparison to a standard Vita shade guide. The Vita shade guide is arranged in the following order (as recommended by the manufacturer) for value assessment: B1*A1*B2*D2*A2*C1*C2*D4*A3*D3*B3*A3.5*B4*C3*A4*C4, where B1 is the brightest and C4 is the darkest. The baseline shade for each tooth ion this example was C4. Data are reported as change in shade value unit ($\Delta$SVU) from baseline.

The data after 30 minutes of total exposure and after 60 minutes total exposure are in Tables 3 and 4, respectively.

TABLE 3

| | 30 minutes total $ClO_2$ exposure | |
|---|---|---|
| | Left: 2 × 15 minutes $\Delta$SVU | Right: 4 × 7.5 minutes $\Delta$SVU |
| Tooth A | 10 | 12 |
| Tooth B | 12 | 12 |
| Tooth C | 11 | 12 |
| Tooth D | 12 | 12 |
| Tooth E | 12 | 15 |
| Average | 11.4 | 12.6 |

TABLE 4

| | 60 minutes total ClO₂ exposure | |
|---|---|---|
| | Left: 4 × 15 minutes ΔSVU | Right: 8 × 7.5 minutes ΔSVU |
| Tooth A | 12 | 14 |
| Tooth B | 12 | 12 |
| Tooth C | 11 | 12 |
| Tooth D | 12 | 15 |
| Tooth E | 12 | 15 |
| Average | 11.8 | 13.6 |

These data demonstrate that for a given total exposure time, more frequent administration of substantially contiguous applications of freshly-made chlorine dioxide composition yields a marked improvement in tooth whitening. Specifically, administration of a nominal dosage of 6000 ppm-min (30 minutes exposure×200 ppm) in four applications improved tooth whitening by about 10% compared to administration of 6000 ppm-min in two applications. Similarly, administration of a nominal dosage of 12,000 ppm-min in eight applications improved tooth whitening by about 15% over administration in four applications.

Based on these data, it is expected that administration of chlorine dioxide by continuous irrigation would yield better whitening results compared to the results achieved by applying chlorine dioxide composition on a tray for the same duration as the continuous treatment.

The disclosures of each and every patent, patent application, and publication cited herein are hereby incorporated herein by reference in their entirety.

While the compositions, kits, and their methods of use have been disclosed with reference to specific embodiments, it is apparent that other embodiments and variations may be devised by others skilled in the art without departing from the true spirit and scope of the described compositions, kits and methods of use. The appended claims are intended to be construed to include all such embodiments and equivalent variations.

What is claimed is:

1. A method for treating a wound in a tissue, the method comprising administering to the wound a composition comprising a chlorine dioxide source to provide an efficacious amount of chlorine dioxide to the wound, thereby treating the wound,
   wherein the administering step comprises one of:
   i) contacting the wound with a composition comprising the chlorine dioxide source and oxy-chlorine anions, wherein the composition comprises no more than about 0.25 milligrams oxy-chlorine anion per gram composition and is a substantially non-cytotoxic composition:
   ii) contacting the wound with a device comprising the chlorine dioxide source and oxy-chlorine anions, wherein the device delivers a substantially oxy-chlorine anion free chlorine dioxide composition comprising no more than about 0.25 milligrams oxy-chlorine anion per gram composition to the wound; or
   iii) contacting the wound with a composition comprising the chlorine dioxide source and oxy-chlorine anions; and
      a barrier substance that substantially prohibits passage therethrough of the oxy-chlorine anions and permits passage therethrough of a substantially oxy-chlorine anion free chlorine dioxide composition comprising more than about 0.25 milligrams oxy-chlorine anion per gram composition, thereby delivering the substantially oxy-chlorine anion free chlorine dioxide composition to the wound.

2. The method of claim 1, further comprising a second iteration of the contacting step, wherein the second iteration is substantially contiguous with the first iteration.

3. The method of claim 2, further comprising at least a third iteration of the contacting step, wherein the third iteration is substantially contiguous with the second iteration.

4. The method of claim 1, wherein the administration step comprises i) contacting the wound with the composition comprising the chlorine dioxide source and oxy-chlorine anions to form a composition-contacted wound.

5. The method of claim 1, wherein the administration step comprises i) contacting the wound with the composition comprising the chlorine dioxide source and oxy-chlorine anions by irrigating the wound with the composition using an irrigation device.

6. The method of claim 1, wherein the administration step comprises ii) contacting the wound with the device comprising the chlorine dioxide source and oxy-chlorine anions, wherein the device is an irrigation device that delivers a substantially oxy-chlorine anion free chlorine dioxide composition comprising no more than about 0.25 milligrams oxy-chlorine anion per gram composition to the wound.

7. The method of claim 6, wherein the administration step comprises contacting the wound with the device comprising the chlorine dioxide source and oxy-chlorine anions to form a device-contacted wound, and further comprising applying ultrasonic energy to the device-contacted wound.

8. The method of claim 1 wherein the administration step comprises iii) contacting the wound with the composition comprising the chlorine dioxide source and oxy-chlorine anions; and the barrier substance that substantially prohibits passage therethrough of the oxy-chlorine anions and permits passage therethrough of a substantially oxy-chlorine anion free chlorine dioxide composition to form a composition-contacted wound.

9. The method of claim 1, wherein the composition comprising the chlorine dioxide source comprises about 1 to about 1000 ppm chlorine dioxide.

10. The method of claim 1, wherein the composition comprising the chlorine dioxide source has a pH from about 4.5 to about 11.

11. The method of claim 1, wherein an actual dosage of at least about 200 ppm-minutes of chlorine dioxide is administered.

12. The method of claim 4, wherein the ultrasonic energy frequency is between about 10 kHz to about 100 kHz with a power intensity of about 2 W/cm² to about 3.5 W/cm².

13. The method of claim 4, further comprising applying ultrasonic energy to the composition-contacted wound.

14. The method of claim 8, further comprising applying ultrasonic energy to the composition-contacted wound.

15. The method of claim 4, further comprising at least a second administering step, wherein the second administering step comprises one of
   ii) contacting the wound with a device comprising a chlorine dioxide source and oxy-chlorine anions, wherein the device delivers a substantially oxy-chlorine anion free chlorine dioxide composition comprising no more than about 0.25 milligrams oxy-chlorine anion per gram composition to the tissue; or
   iii) contacting the wound with a composition comprising a chlorine dioxide source and oxy-chlorine anions; and a barrier substance that substantially prohibits passage therethrough of the oxy-chlorine anions and permits passage therethrough of a substantially oxy-chlorine anion free chlorine dioxide composition comprising no more than about 0.25 milligrams oxy-chlorine anion per gram composition, thereby delivering the substantially oxy-chlorine anion free chlorine dioxide composition to the wound.

16. The method of claim 6, further comprising at least a second administering step, wherein the second administering step comprises one of
   i) contacting the wound with a composition comprising a chlorine dioxide source and oxy-chlorine anions, wherein the composition comprises no more than about 0.25 milligrams oxy-chlorine anion per gram composition and is a substantially non-cytotoxic composition; or
   iii) contacting the wound with a composition comprising a chlorine dioxide source and oxy-chlorine anions; and
   a barrier substance that substantially prohibits passage therethrough of the oxy-chlorine anions and permits passage therethrough of a substantially oxy-chlorine anion free chlorine dioxide composition comprising no more than about 0.25 milligrams oxy-chlorine anion per gram composition, thereby delivering the substantially oxy-chlorine anion free chlorine dioxide composition to the wound.

17. The method of claim 8, further comprising at least a second administering step, wherein the second administering step comprises one of
   i) contacting the wound with a composition comprising a chlorine dioxide source and oxy-chlorine anions, wherein the composition comprises no more than about 0.25 milligrams oxy-chlorine anion per gram composition and is a substantially non-cytotoxic composition; or
   ii) contacting the wound with a device comprising a chlorine dioxide source and oxy-chlorine anions, wherein the device delivers a substantially oxy-chlorine anion free chlorine dioxide composition comprising no more than about 0.25 milligrams oxy-chlorine anion per gram composition to the tissue.

* * * * *